United States Patent
Narayanan et al.

(10) Patent No.: US 10,010,598 B2
(45) Date of Patent: Jul. 3, 2018

(54) **COMPOSITIONS AND METHODS FOR DETECTING, TREATING, AND PROTECTING AGAINST *FUSOBACTERIUM* INFECTION**

(71) Applicant: KANSAS STATE UNIVERSITY RESEARCH FOUNDATION, Manhattan, KS (US)

(72) Inventors: Sanjeev Narayanan, Manhattan, KS (US); Amit Kumar, Manhattan, KS (US); Tiruvoor Nagaraja, Manhatan, KS (US); Muckatira Chengappa, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 15/824,694

(22) Filed: Nov. 28, 2017

(65) Prior Publication Data
US 2018/0071382 A1    Mar. 15, 2018

Related U.S. Application Data

(62) Division of application No. 15/052,594, filed on Feb. 24, 2016, now Pat. No. 9,884,102, which is a division of application No. 14/007,611, filed as application No. PCT/US2012/030576 on Mar. 26, 2012, now Pat. No. 9,308,247.

(60) Provisional application No. 61/467,839, filed on Mar. 25, 2011.

(51) Int. Cl.
*A61K 39/39* (2006.01)
*A61K 39/114* (2006.01)
*C07K 14/195* (2006.01)

(52) U.S. Cl.
CPC ............ *A61K 39/114* (2013.01); *A61K 39/39* (2013.01); *C07K 14/195* (2013.01)

(58) Field of Classification Search
None
See application file for complete search history.

(56) References Cited

PUBLICATIONS

Cheung et al (Can. Fam. Physician, 53:1451-1453, 2007).*

* cited by examiner

*Primary Examiner* — Brian Gangle
(74) *Attorney, Agent, or Firm* — Tracey S. Truitt; Armstrong Teasdale LLP

(57) ABSTRACT

The present invention relates to protecting against, treating, and detecting *Fusobacteria* infections. Compositions and methods derived from nucleic acid and protein sequences of a 40 kDa Adhesin protein are provided to protect against, treat, and detect *Fusobacteria* infections in a subject. In one aspect, vaccines capable of inducing an immune response to a 40 kDa Adhesin protein are used to protect against *Fusobacteria* infection. Also, nucleic acid molecules, proteins, immunogens, antibodies, and antisense molecules derived from the sequences of the 40 kDa Adhesin protein may be used to protect against, treat, and detect *Fusobacteria* infections in a subject.

14 Claims, 20 Drawing Sheets

COMPOSITIONS AND METHODS FOR DETECTING, TREATING, AND PROTECTING AGAINST *FUSOBACTERIUM* INFECTION

FIELD OF THE INVENTION

The present invention relates generally to the field of vaccines for generating protection from infectious disease and infection, and treating symptoms and infections caused by infectious agents, as well as detecting infection of a subject. More specifically, the present invention is useful for protection and treatment of infection by *Fusobacterium* species.

BACKGROUND OF THE INVENTION

*Fusobacterium necrophorum*, a gram negative and rod-shaped anaerobe, is the primary etiologic agent of liver abscesses in ruminant animals, including cattle and sheep. *F. necrophorum* strains are divided into two subspecies, subsp. *necrophorum* (FNN) and subsp. *funduliforme* (FNF). In addition to liver abscesses, the organism is also the primary etiologic agent of foot rot, foot abscesses, calf diphtheria, and is frequently isolated from cases of mastitis, metritis, and necrotic lesions of the oral cavity. It has also been recognized as a human pathogen since the late 1800s. Antibiotics have been used in animal agriculture to treat and prevent fusobacterial infections.

The increasing concern over the use of antibiotics in food animals and its impact on rise of multidrug resistant bacteria has already led to the ban of certain antibiotics in animals. The sub-therapeutic use (i.e., use in the absence of disease) for growth promotion is a practice that is becoming increasingly controversial, since it is implicated as increasing antibiotic resistance among pathogenic bacteria of animals and humans. Additionally, there is a growing demand for natural and organic beef (requirements include cattle be raised without use of antibiotics in feed), which warrants effective vaccines as a method to prevent infections. Accordingly, there is a need to develop an effective vaccine for the prevention of fusobacterial infections, particularly liver abscesses and foot rot.

U.S. Pat. Nos. 5,455,034, 5,492,694, and 5,861,162 describe leukotoxoid vaccines that immunize cattle and sheep against leukotoxin, an important virulence factor, released by *F. necrophorum* after it gains access into the ruminal wall and the liver. While this vaccine reduces the severity and incidence of the disease (by up to 40%) it does not eliminate its occurrence. Moreover, leukotoxoid and bacterin vaccines frequently contain lipopolysaccharides and other cellular derivatives that have side effects (fever, injection site abscesses, etc) and may impact feed-intake and weight gain.

Accordingly, a need still exists for effective prevention and treatment of fusobacterial infections. The present invention provides compositions and methods for effective prevention and treatement of fusobacterial infections.

SUMMARY OF THE INVENTION

The present invention is directed to compositions and methods for effectively preventing and treating *Fusobacteriuml* infections in a subject. The present invention also relates detecting *Fusobacterium* infections.

In one embodiment, the compositions of the invention include isolated nucleic acid molecules. Suitable nucleic acid molecules have a sequence that is at least 60% homologous to SEQ ID NO:1. In some embodiments, the nucleic acid molecule encodes the 40 kDa Adhesin protein ("Adhesin") of SEQ ID NO: 2. In some embodiments, the nucleic acid molecule encodes a portion of the Adhesin protein. Such partial coding may be used as antisense sequence to inhibit Adhesin protein, as molecular probes to detect Adhesin protein, or as primers in cloning techniques. Preferably, the nucleic acid molecule has a sequence that is about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99%, or more homologous to the sequence of SEQ ID NO: 1. More preferably, the nucleic acid molecule has a sequence that is at least 65% homologous to SEQ ID NO: 1.

The nucleic acid molecules of the invention may be within a vector. Suitable vectors include those used for cloning, expression, and propagating.

In some embodiments the nucleic acid molecules encode a protein, or portion thereof, having at least 60% sequence homology with SEQ ID NO:2, or portion thereof. Preferably, the nucleic acid molecules encode a protein, or portion thereof, that is about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99%, or more homologous to the sequence of SEQ ID NO: 2, or portion thereof. More preferably, the nucleic acid molecules encode a protein, or portion thereof, that is at least 65% homologous to SEQ ID NO: 2, or portion thereof.

In another embodiment, the compositions of the invention include an immunogenic composition containing an isolated protein having at least 60% sequence homology to SEQ ID NO:2 and a pharmaceutically acceptable carrier. The isolated protein may encode a partial protein sequence. Such a partial sequence may be 5 to 356 amino acids in length. Preferably, the partial protein sequence is capable of inducing an immune response in a subject. Such partial peptide sequences of SEQ ID NO:2 include any partial sequence of SEQ ID NO:2 as well as those of SEQ ID NO: 3-5 and 8-17. Preferably, the partial sequence is SEQ ID NO: 9.

In some embodiments, the immunogenic composition includes a leukotoxin immunogen. Suitable leukotoxin immunogens include recombinant leukotoxin protein, partial recombinant leukotoxin peptides, leukotoxin protein isolated from secretions of *Fusobacterium* and combinations thereof.

In one aspect, the present invention includes methods of immunizing a subject against *Fusobacterium* infection. In one embodiment, the methods of immunizing include a method of inducing an immune response in a subject specific for infection by *Fusobacterium* where a subject is administered an Adhesin agent. Suitable Adhesin agents include antibodies, immunogens, antisense molecules, small molecules, or combinations thereof. Suitable immunogens include isolated proteins having at least 60% sequence homology with SEQ ID NO: 2 or partial peptide sequences thereof. Such partial peptide sequences of SEQ ID NO:2 include any partial sequence of SEQ ID NO:2 as well as those of SEQ ID NO: 3-5 and 8-17. In another embodiment, the invention provides a method of reducing the incidence of or severity of clinical signs or symptoms caused by infection by *Fusobacterium* where a subject is administered an Adhesin agent. The Adhesin agent may be provided in a pharmaceutically acceptable carrier. In some embodiments, the pharmaceutically acceptable carrier includes an adjuvant. In some embodiments, the subject is not infected with

*Fusobacterium*. In other embodiments, the subject is infected with *Fusobacterium*. In some embodiments, the incidence of symptoms is reduced an amount ranging from about 5% to 100% when compared to a control not receiving an Adhesin agent. Preferably, the incidence of symptoms is reduced an amount of about 10, 15, 20, 25, 30, 35, 40, 45, 50, 55, 60, 65, 70, 75, 80, 85, 90, 95% or more when compared to a control not receiving an Adhesin agent. More preferably, the incidence of symptoms is reduced an amount of about 10% when compared to a control not receiving an Adhesin agent. In some embodiments, the incidence of symptoms is reduced as to a specific subject. In some embodiments, the incidence of symptoms is reduced as to a group of subjects. In some embodiments, the incidence of symptoms is reduced as to a herd of subjects.

In another aspect, the present invention includes methods of decreasing the mortality rate of infection with *Fusobacterium* where a subject is administered an Adhesin agent. The Adhesin agent may be provided in a pharmaceutically acceptable carrier. In some embodiments, the pharmaceutically acceptable carrier includes an adjuvant. In some embodiments, the subject is not infected with *Fusobacterium*. In other embodiments, the subject is infected with *Fusobacterium*. In some embodiments, the mortality rate is decreased about 5% to 100% when compared to a control not receiving an Adhesin agent. Preferably, the mortality rate is decreased about 10, 15, 20, 25, 30, 35, 40, 45, 50, 55, 60, 65, 70, 75, 80, 85, 90, 95% or more when compared to a control not receiving an Adhesin agent. More preferably, the mortality rate is decreased about 10% when compared to a control not receiving an Adhesin agent. In some embodiments, the mortality rate is decreased as to a specific subject. In some embodiments, the mortality rate is decreased as to a group of subjects. In some embodiments, the mortality rate is decreased is reduced as to a herd of subjects.

In another aspect, the present invention includes methods of detecting infection with *Fusobacterium*. Methods of detecting *Fusobacterium* infection include obtaining a sample from a subject, contacting the sample with an Adhesin indicator, and detecting the Adhesin indicator. Suitable Adhesin indicators include proteins, antibodies, antisense molecules, and small molecules capable of binding to Adhesin or a coding sequence thereof. Preferably, the Adhesin indicators are labeled with a detection label, such as a fluorescence label, radiotype label, chemical label, or other label known or used in the art with detection assays.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 graphically illustrates the binding between subsp. *necrophorum* (FNN) (1) and subsp. *funduliforme* (FNF) (2) to bovine adrenal capillary endothelial (EJG) cells;

FIG. 2A depicts transmission electron microscope (TEM) images (negatively stained) of *Fusobacterium necrophorum* subsp. *necrophorum* (FNN) from cattle;

FIG. 2B depicts transmission electron microscope (TEM) images (positively stained) of *Fusobacterium necrophorum* subsp. *necrophorum* (FNN) from cattle;

FIG. 2C depicts transmission electron microscope (TEM) images (negatively stained) of *Fusobacterium necrophorum* subsp. *funduliforme* (FNF) isolates from humans;

FIG. 2D depicts transmission electron microscope (TEM) images (positively stained) of *Fusobacterium necrophorum* subsp. *funduliforme* (FNF) isolates from humans;

FIG. 3 shows the outer membrane protein (OMP) profiles of subsp. *Necrophorum* (FNN) (Lanes 1 and 2) and subspecies *funduliforme* (FNF) (Lanes 4 and 5; Lane 3 is a molecular weight marker);

FIG. 4 graphically illustrates the attachment of FNN to EJG cells (1). The attachment reduced significantly when pretreated with polyclonal antisera raised against the OMPs of FNN (2). The attachment did not reduce when pretreated with polyclonal antisera raised against OMPs of FNF (3). The attachment reduced significantly when EJG cells were pretreated with subsp. *necrophorum* OMPs (4) or with 40 kDa adhesin (5);

FIG. 5 shows an SDS-PAGE of serial steps in purification of a 40 kDa adhesin from cattle strain of FNN. Key: Lane 2, total unbound OMP removed from the well; Lane 3, PBS wash; Lane 4, PBS+NP40; Lane 5, Modified RIPA; Lane 6, SDS sample buffer; Lane 8, western-blot of lane 6 with antisera for OMPs of cattle FNN; Lane 9, western-blot with antisera for OMPs of cattle FNF; Lane 11, far-western with biotinylated fibronectin; and, Lanes 1, 7 and 10 are molecular weight markers;

FIG. 6 shows the 40 kDa adhesion is present in human *F. necrophorum* strains. Key: Lane 1, 1 kb DNA ladder; Lanes 2-5, human strains; Lane 6, subsp. *necrophorum*, cattle; Lane 7, subsp. *funduliforme*, cattle; and Lane 8, negative control;

FIG. 7 shows a western blot confirming the expression of 40 kDa adhesin in *E. coli* BL21(DE3) cells transfected with a vector containing the 40 kDa coding sequence (SEQ ID NO: 6). Key: Lane 1, uninduced *E. coli*; Lanes 2-6, induced *E. coli* expressing the encoded 40 kDa protein;

FIG. 8 shows the 40 kDa adhesion protein adheres to EJG cells. The EJG cells are the polygonal cells containing dark round nuclei. The 40 kDa is the bright white blurred spots covering the polygonal cells;

FIG. 9 shows attachment of *F. necrophorum* subsp. *necrophorum* (FNN) to Bovine Capillary Endothelial (EJG) cells. The EJG cells are polygonal shaped cells with dark round nuclei contained within. The attached FNN are dark spots on the EJG cells;

FIG. 10 shows an SDS-PAGE of serial steps in purification of a 40 kDa adhesion. Key: Lane 2, Total unbound OMP removed from the well; PBS wash, Lane 3 treated, Lane 4 untreated; PBS+NP40, Lane 5 treated, Lane 6 untreated; Modified RIPA, Lane 7 treated, Lane 8 untreated; SDS sample buffer, Lane 10 treated, Lane 11 untreated; and, Lane 1 marker;

FIG. 11A shows the presence of 40 kDa adhesin in different strains of subsp. *necrophorum* (Lane 1:A25, Lane 2: A21, Lane 3: A50, Lane 4: 8L1) and subsp. *funduliforme* (Lane 6: B17, Lane 7:629, Lane 8:647, Lane 9: B35). Lane 5 is a 1 kb DNA ladder;

FIG. 11B shows the presence of 40 kDa adhesin in human *F. necrophorum* strains (Lane 1: 1 kb DNA ladder, Lanes 2-5: human strains, Lane 6: subsp. *necrophorum*, Lane 7: subsp. *funduliforme*, and Lane 8: negative control);

FIG. 12 shows the presence of fibronectin in EJG cell culture. The dark ovals represent DAPI staining of cell nuclei, while the white elongated staining is the fibronectin;

FIG. 13 shows a Far-western analysis of the 40 kDa FncA Adhesin with bovine fibronectin. The biotinylated fibronectin bound to the purified FncA (1) and not the control (2);

FIG. 14 shows an SDS-PAGE of serial steps in purification of a 40 kDa adhesion. Key: Lane 2, Total OMP removed from the well; 3, PBS wash; 4, PBS+NP40; 5, Modified RIPA; 6, SDS sample buffer; 8, western blot of lane 6 with antisera for total OMPs of FNN; 9, western blot of lane 6 with antisera for total OMPs of FNF; Lanes 1 and 7 are molecular weight markers;

FIG. 15 graphically illustrates that attachment of FNN to EJG cells was reduced significantly when FNN was pretreated with antiserum raised against the 40 kDa adhesion of FNN (3) compared to no serum (1) or pretreatment with pre-vaccination serum (2);

DETAILED DESCRIPTION

Figure 1:
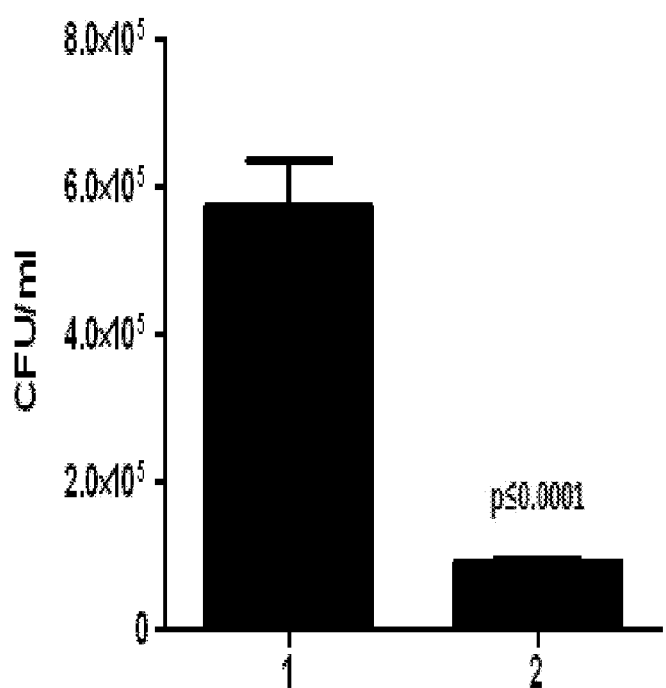

Applicants have discovered a protein that plays a pivotal role in mediating *Fusobacterium* attachment to host cells allowing pathologic infection of a host. The present invention encompasses this discovery and provides compositions and methods based on the discovered protein and attachment mechanism. In particular, the present invention provides compositions and methods useful in research, diagnostics, and therapeutics for conditions and diseases associated with pathologic infection of *Fusobacterium necrophorum*. The compositions and methods are directed at inducing an immune response in a subject to protect against, or treat, Fusobacterium infection, as well as detection of *Fusobacterium*.

Various aspects of the invention are described in further detail in the following subsections.

I. Compositions

A. Nucleic Acid Molecules

One aspect of the invention pertains to isolated nucleic acid molecules that encode Adhesin proteins or biologically active portions thereof, as well as nucleic acid molecules sufficient for use as hybridization probes to identify Adhesin-encoding nucleic acids (e.g., Adhesin mRNA) and fragments for use as PCR primers for the amplification or mutation of Adhesin nucleic acid molecules.

A nucleic acid molecule of the present invention, e.g., a nucleic acid molecule having the nucleotide sequence of SEQ ID NO:1, or a complement thereof, may be isolated using standard molecular biology techniques and the sequence information provided herein. Using all or portion of the nucleic acid sequence of SEQ ID NO:1, Adhesin nucleic acid molecules may be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

A nucleic acid of the invention may be amplified using cDNA, mRNA or genomic DNA as a template and appropriate oligonucleotide primers according to standard PCR amplification techniques. The nucleic acid so amplified may be cloned into an appropriate vector and characterized by DNA sequence analysis. Furthermore, oligonucleotides corresponding to Adhesin nucleotide sequences may be prepared by standard synthetic techniques known in the art, such as using an automated DNA synthesizer.

In another embodiment, an isolated nucleic acid molecule of the invention comprises a nucleic acid molecule which is a complement of the nucleotide sequence shown in SEQ ID NO:1, or portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention may comprise only a portion of a nucleic acid sequence encoding Adhesin. By way of example, a fragment of the nucleic acid coding sequence can be used as a probe, primer, or a fragment encoding a biologically active portion of Adhesin. The nucleotide sequence determined from the cloning of the Adhesin gene allows for the generation of probes and primers designed for use in identifying and/or cloning Adhesin homologues in other cell types, as well as Adhesin homologues and orthologs from other mammals. The probe/primer typically comprises substantially purified oligonucleotide. The oligonucleotide typically comprises a region of nucleotide sequence that hybridizes under stringent conditions to at least about 12, 13, 14, 15, 16, 17, 18, 19, 20, 21, 22, 23, or 24; preferably about 25, 26, 27, 28, 29, 30, 31, 32, 33, 34, 35, 36, 37, 38, 39, 40, 41, 42, 43, 44, 45, 46, 47, 48, or 49; more preferably about 50, 75, 100, 125, 150, 175, 200, 250, 300, 350 or 400 consecutive nucleotides of the sense or antisense sequence of SEQ ID NO:1, or of a naturally occurring mutant of SEQ ID NO:1.

Probes based on the Adhesin nucleotide sequence may be used to detect transcripts or genomic sequences encoding the same or similar proteins. The probe comprises a label group attached thereto, such as a radioisotope, a fluorescent compound, an enzyme, or an enzyme co-factor. Such probes may be used in diagnostic or screening assays and include those known in the art or yet to be discovered.

A nucleic acid fragment encoding a "biologically active portion" of Adhesin may be prepared by isolating a portion of SEQ ID NO:1, which encodes a polypeptide having a Adhesin biological activity, expressing the encoded portion of Adhesin protein (e.g., by recombinant expression in vitro) and assessing the activity of the encoded portion of Adhesin. For example, a nucleic acid fragment encoding a biologically active portion of Adhesin includes a host cell binding domain. Suitable nucleic acid fragments may encode biologically active portions of Adhesin such as those of SEQ ID NO: 3-5 and 8-17.

The invention further encompasses nucleic acid molecules that differ from the nucleotide sequence of SEQ ID NO:1, due to degeneracy of the genetic code and thus encode the same Adhesin protein as that encoded by the nucleotide sequence shown in SEQ ID NO:1.

In addition to the Adhesin nucleotide sequence shown in SEQ ID NO:1, it will be appreciated by those skilled in the art that DNA sequence polymorphisms that lead to changes in the amino acid sequences of Adhesin may exist. Such genetic polymorphism in the Adhesin gene may exist among bacteria within a subspecies due to natural allelic variation. Such natural allelic variations typically result in 15% variance in the nucleotide sequence of the Adhesin gene. Any and all such nucleotide variations and resulting amino acid polymorphisms in Adhesin that are the result of natural allelic variation and that do not alter the functional activity of Adhesin are intended to be within the scope of the invention. Thus, e.g., 1%, 2%, 3%, 4%, or 5% of the amino acids in Adhesin (e.g., 1, 2, 3, 4, 5, 6, 8, 10, 15, 20, 25, 30, 35, 40, 45, 50, or 55 amino acids) may be replaced by another amino acid, preferably by conservative substitution.

Moreover, nucleic acid molecules encoding Adhesin proteins from other species (Adhesin orthologs/homologues), which have a nucleotide sequence which differs from that of an Adhesin disclosed herein, are intended to be within the scope of the invention.

Accordingly, in another embodiment, an isolated nucleic acid molecule of the invention is at least about 12 to 1075 (15, 20, 25, 30, 35, 40, 45, 50, 55, 60, 65, 70, 75, 80, 85, 90, 100, 150, 200, 250, 300, 325, 350, 375, 400, 425, 450, 500, 550, 600, 650, 700, 800, 900, 1000, and 1071) nucleotides in length and hybridizes under stringent conditions to the nucleic acid molecule comprising the nucleotide sequence, preferably the coding sequence, of SEQ ID NO:1.

In addition to naturally occurring allelic variants of the Adhesin sequence that may exist in the population, the skilled artisan will further appreciate that changes may be introduced by mutation into the nucleotide sequence of SEQ ID NO:1, thereby leading to changes in the amino acid sequence of the encoded protein without altering the functional ability of the protein. For example, such mutations may include nucleotide substitutions leading to amino acid substitutions at "unnecessary" amino acid residues. An "unnecessary" amino acid residue is a residue that may be altered from the wildtype sequence of Adhesin protein without altering the biological activity, whereas an "necessary" amino acid residue is required for biological activity.

Accordingly, another aspect of the invention pertains to nucleic acid molecules encoding Adhesin proteins that contain changes in amino acid residues that may or may not be essential for activity. Such Adhesin proteins differ in amino acid sequence from SEQ ID NO: 2. In one embodiment, the isolated nucleic acid molecule includes a nucleotide sequence encoding a protein that includes an amino acid sequence that is at least about 45% identical, 65%, 75%, 85%, 95%, 98% or more identical to the amino acid sequence of SEQ ID NO:2. An isolated nucleic acid molecule encoding an Adhesin protein having a sequence which differs from that of SEQ ID NO:2, may be created by introducing one or more nucleotide substitutions, additions or deletions into the nucleotide sequence of Adhesin (SEQ ID NO:1) such that one or more amino acid substitutions, additions or deletions are introduced into the encoded protein. Mutations may be introduced by standard techniques known in the art, such as site-directed mutagenesis and PCR-mediated mutagenesis.

The present invention encompasses antisense nucleic acid molecules. Antisense molecules are complementary to a sense nucleic acid encoding a protein, complementary to the coding strand of a double-stranded cDNA molecule, or complementary to an mRNA sequence. Accordingly, an antisense nucleic acid hydrogen bonds to a sense nucleic acid. The antisense nucleic acid can be complementary to an entire Adhesin coding strand, or to only a portion thereof, such as all or part of the protein coding region (or open reading frame). An antisense nucleic acid molecule can be antisense to a noncoding region of the coding strand of a nucleotide sequence encoding Adhesin. The noncoding regions ("5' and 3' untranslated regions") are the 5' and 3' sequences that flank the coding region and are not translated into amino acids. Given the coding strand sequences encoding Adhesin disclosed herein, antisense nucleic acids of the invention may be designed according to the rules of Watson and Crick base pairing. The antisense nucleic acid molecule may be complementary to the entire coding region of Adhesin mRNA, but more preferably is an oligonucleotide which is antisense to only a portion of the coding or noncoding region of Adhesin mRNA. For example, the antisense oligonucleotide may be complementary to the region surrounding the translation start site of Adhesin mRNA. An antisense oligonucleotide may be, for example, about 5, 10, 15, 20, 25, 30, 35, 40, 45 or 50 nucleotides in length. An antisense nucleic acid of the invention may be constructed using chemical synthesis and enzymatic ligation reactions using procedures known in the art. For example, an antisense nucleic acid (e.g., an antisense oligonucleotide) may be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which may be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino-3-N-2-carboxypropyl) uracil, (acp3)w, and 2,6-diaminopurine. Alternatively, the antisense nucleic acid may be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an Adhesin protein to thereby inhibit expression of the protein, e.g., by inhibiting transcription and/or translation. The hybridization may be by conventional nucleotide complementarity to form a stable duplex, or, for example, in the case of an antisense nucleic acid molecule which binds to DNA duplexes, through specific interactions in the major groove of the double helix. An antisense nucleic acid molecule of the invention may be administered by direct injection at a tissue site. Alternatively, antisense nucleic acid molecules may be modified to target selected cells and then administered systemically. For example, for systemic administration, antisense molecules may be modified such that they specifically bind to receptors or antigens expressed on a selected cell surface, e.g., by linking the antisense nucleic acid molecules to peptides or antibodies which bind to cell surface receptors or antigens. The antisense nucleic acid molecules may also be delivered to cells using the plasmids described herein. To achieve sufficient intracellular concentrations of the antisense molecules, plasmid constructs in which the antisense nucleic acid molecule is placed under the control of a strong pol II or pol III promoter are preferred.

B. Adhesin Proteins

One aspect of the invention pertains to isolated Adhesin proteins, and biologically active portions thereof, as well as polypeptide fragments suitable for use as immunogens to raise anti-Adhesin antibodies. In one embodiment, native Adhesin proteins may be isolated from cells or tissue sources by an appropriate purification scheme using standard protein purification techniques. In another embodiment, Adhesin proteins are produced by recombinant DNA techniques. Alternative to recombinant expression, an Adhesin protein or polypeptide may be synthesized chemically using standard peptide synthesis techniques.

An "isolated" or "purified" protein or biologically active portion thereof is substantially free of cellular material or other contaminating proteins from the cell or tissue source from which the Adhesin protein is derived, or substantially free from chemical precursors or other chemicals when chemically synthesized. The language "substantially free of cellular material" includes preparations of Adhesin protein in which the protein is separated from cellular components of the cells from which it is isolated or recombinantly produced. Thus, Adhesin protein that is substantially free of cellular material includes preparations of Adhesin protein having less than about 30%, 20%, 10%, or 5% (by dry weight) of non-Adhesin protein (also referred to herein as a "contaminating protein"). When the Adhesin protein or biologically active portion thereof is recombinantly produced, it is also preferably substantially free of culture medium, i.e., culture medium represents less than about 20%, 10%, or 5% of the volume of the protein preparation. When Adhesin protein is produced by chemical synthesis, it is preferably substantially free of chemical precursors or other chemicals, i.e., it is separated from chemical precursors or other chemicals which are involved in the synthesis of the protein. Accordingly, such preparations of Adhesin protein have less than about 30%, 20%, 10%, 5% (by dry weight) of chemical precursors or non-Adhesin chemicals.

Biologically active portions of a Adhesin protein include peptides comprising amino acid sequences sufficiently identical to or derived from the amino acid sequence of the Adhesin protein (e.g., the amino acid sequence shown in SEQ ID NO:2), which include less amino acids than the full length Adhesin protein, and exhibit at least one activity of a Adhesin protein. Typically, biologically active portions comprise a domain or motif with at least one activity of the Adhesin protein. A biologically active portion of an Adhesin protein may be a polypeptide which is, for example, 10, 25, 50, 100, 150, 200, 250, 300 or more amino acids in length. Preferred biologically active polypeptides include one or more identified Adhesin structural domains, such as host cell attachment domain and other domains that may be discovered. Such biologically active portions of Adhesin protein are those of SEQ ID NO: 3-5 and 8-17.

Moreover, other biologically active portions, in which other regions of the protein are deleted, may be prepared by recombinant techniques and evaluated for one or more of the functional activities of a native Adhesin protein.

The Adhesin protein has the amino acid sequence of SEQ ID NO:2. Other useful Adhesin proteins are substantially identical to SEQ ID NO:2 and retain the functional activity of the protein of SEQ ID NO:2, yet differ in amino acid sequence due to natural allelic variation or mutagenesis.

A useful Adhesin protein is a protein which includes an amino acid sequence at least about 45%, preferably 55%, 65%, 75%, 85%, 95%, or 99% identical to the amino acid sequences of SEQ ID NO:2, 3-5, or 8-17. In some embodiments, a useful Adhesin protein is a protein which includes an amino acid sequence at least about 45%, preferably 55%, 65%, 75%, 85%, 95%, or 99% identical to the amino acid sequences of SEQ ID NO:2, 3-5, or 8-17 and retains the functional activity of the Adhesin protein of SEQ ID NO:2, 3-5, or 8-17. Preferably, the sequence is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more identical to the amino acid sequence of SEQ ID NO:2, 3-5, or 8-17. More preferably, the sequence is about 55, 56, 57, 58, 59, 60, 61, 62, 63, 64, 65, 66, 67, 68, 69, 70% or more identical to the amino acid sequence of SEQ ID NO:2, 3-5, or 8-17. More preferably, the sequence is about 60% identical to the amino acid sequence of SEQ ID NO:2, 3-5, or 8-17.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions.times.100).

The determination of percent homology between two sequences may be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264-2268, modified as in Karlin and Altschul (1993) Proc. Nat'l Acad. Sci. USA 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12 to obtain nucleotide sequences similar or homologous to Adhesin nucleic acid molecules of the invention. To obtain gapped alignments for comparison purposes, Gapped BLAST can be utilized as described in Altschul et al. (1997) Nucleic Acids Res. 25:3389-3402. When utilizing BLAST and Gapped BLAST programs, the default parameters of the respective programs (e.g., XBLAST and NBLAST) can be used.

The invention also provides Adhesin chimeric or fusion proteins. As used herein, an Adhesin "chimeric protein" or "fusion protein" comprises an Adhesin polypeptide operatively linked to a non-Adhesin polypeptide. An "Adhesin polypeptide" refers to a polypeptide having an amino acid sequence corresponding to all or a portion (preferably a biologically active portion) of a Adhesin, whereas a "non-Adhesin polypeptide" refers to a polypeptide having an amino acid sequence corresponding to a protein which is not substantially identical to a Adhesin protein. Within the fusion protein, the term "operatively linked" is intended to indicate that the Adhesin polypeptide and the non-Adhesin polypeptide are fused in-frame to each other. The heterologous polypeptide may be fused to the N-terminus or C-terminus of the Adhesin polypeptide.

One useful fusion protein is a GST fusion protein in which the Adhesin sequences are fused to the C-terminus of the GST sequences. Such fusion proteins can facilitate the purification of recombinant Adhesin.

In yet another embodiment, the fusion protein is an Adhesin-immunoglobulin fusion protein in which all or part of Adhesin is fused to sequences derived from a member of the immunoglobulin protein family. The Adhesin-immunoglobulin fusion proteins of the invention may be incorporated into pharmaceutical compositions and administered to a subject to inhibit an interaction between Adhesin protein and Adhesin targets, such as a host cell, to thereby suppress Adhesin activity in vivo. Inhibition of the Adhesin target/Adhesin interaction may be useful therapeutically for both the treatment of bacterial infections of *Fusobacterium*, as well as prevention of pathologic disease caused by *Fusobacterium*. Moreover, the Adhesin-immunoglobulin fusion proteins of the invention may be used as immunogens to produce anti-Adhesin antibodies in a subject, to purify Adhesin ligands, in detection assays to detect the presence of *Fusobacterium* and in screening assays to identify molecules which inhibit the interaction of Adhesin with an Adhesin target.

Preferably, an Adhesin chimeric or fusion protein of the invention is produced by standard recombinant DNA techniques. For example, DNA fragments coding for the different polypeptide sequences are ligated together in-frame in accordance with conventional techniques. Suitable techniques include by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). An Adhesin-encoding nucleic acid may be cloned into such an expression vector such that the fusion moiety is linked in-frame to the Adhesin protein.

The present invention also pertains to variants of the Adhesin proteins which function as Adhesin antagonists. Variants of the Adhesin proteins may be generated by mutagenesis techniques known in the art. An antagonist of the Adhesin protein may inhibit one or more of the activities of the naturally occurring form of the Adhesin protein by, for example, competitively binding to a downstream or upstream member of a cellular signaling cascade which includes the Adhesin protein, or by inhibiting binding to Adhesin targets. Thus, specific biological effects may be elicited by treatment with a variant of limited function. Treatment of a subject with a variant having a subset of the biological activities of the naturally occurring form of the protein may have fewer side effects in a subject relative to treatment with the naturally occurring form of the Adhesin proteins.

Variants of the Adhesin protein which function as Adhesin antagonists can be identified by screening combinatorial libraries of mutants, such as truncation mutants of the Adhesin protein for Adhesin antagonist activity. In one embodiment, a variegated library of Adhesin variants is generated by combinatorial mutagenesis at the nucleic acid level and is encoded by a variegated gene library. A variegated library of Adhesin variants may be produced by, for example, enzymatically ligating a mixture of synthetic oligonucleotides into gene sequences such that a degenerate set of potential Adhesin sequences is expressible as individual polypeptides, or alternatively, as a set of larger fusion proteins (e.g., for phage display) containing the set of Adhesin sequences therein. There are a variety of methods which may be used to produce libraries of potential Adhesin variants from a degenerate oligonucleotide sequence. Chemical synthesis of a degenerate gene sequence may be performed in an automatic DNA synthesizer, and the synthetic gene then ligated into an appropriate expression vector. Use of a degenerate set of genes allows for the provision, in one mixture, of all of the sequences encoding the desired set of potential Adhesin sequences. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the Adhesin protein coding sequence can be used to generate a variegated population of Adhesin fragments for screening and subsequent selection of variants of a Adhesin protein. In one embodiment, a library of coding sequence fragments can be generated by treating a double stranded PCR fragment of a Adhesin coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the Adhesin protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Adhesin proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify Adhesin variants (Arkin and Yourvan (1992) Proc. Natl. Acad. Sci. USA 89:7811-7815; Delgrave et al. (1993) Protein Engineering 6(3):327-331).

C. Expression Systems

In one aspect, the sequences of the invention may be incorporated into an expression system. Many expression systems are known in the art and are contemplated herein. Suitable expression systems include those that use an expression vector. Suitable expression vectors include regulatory sequences, operably linked to the sequences of the invention, that permit transcription and translation of the coding sequence. Exemplary regulatory sequences include, without limitation, promoters, enhancers, terminators, operators, repressors, inducers, and other regulatory elements known in the art. Expression vectors generally have convenient restriction sites located near the promoter sequence to provide for the insertion of nucleic acid sequences. Also, selectable markers operative in the expression host may be included in the expression vector. Any expression vector known in the art or yet to be discovered may be used with the coding sequences of the invention. A skilled artisan will recognize that the choice of vector for use with the invention is dependent on the intended use as well as the host within which the coding sequence is to be expressed. Suitable vectors include, but are not limited to, bacteriophage-derived vectors, viral vectors, retroviral vectors, adenoviral vectors, prokaryotic expression vectors, and eukaryotic expression vectors. In some embodiments, an expression vector capable of prokaryotic expression is preferred. In other embodiments, an expression vector capable of eukaryotic expression is preferred. In yet other embodiments, an expression vector capable of both prokaryotic and eukaryotic expression is preferred. In one aspect, an inducible expression vector is preferred. Suitable inducible expression vectors include those known in the art that activate transcription only in the presence of a specific inducer (e.g. isopropyl thiogalactopyranoside (IPTG), hormone-based inducers such as progesterone, antibiotic-based inducers such as tetracycline, etc.). Preferably, the expression vector includes a T7 promoter. Exemplary vectors include, without limitation, pET vectors, pET31b, pET32, pET22b, pLac1, pLysE, pLysS, and others known in the art. More preferably, the expression vector is pET22b.

Expression vectors may be used with any compatible host cell. The expression vector may exist in a host cell as an extrachromosomal element or integrated into the host genome. Host cells may be prokaryotic, such as any number of bacteria strains, or may be eukaryotic, such as yeast or other fungal cells, insect, plant, amphibian, or mammalian cells, including rodent, animal or human cells. In one aspect, it is preferred that the host cells are prokaryotic. Suitable prokaryotic cells include a number of bacteria strains including strains of *E. coli*. Preferably, the host cell is *E. coli* DH5a, *E. coli* BL21, or any other bacteria known in the art. More preferably, the host cell is *E. coli* BL21.

D. Antibodies

An isolated Adhesin protein, or a portion or fragment thereof, can be used as an immunogen to generate antibodies that bind Adhesin using standard techniques for polyclonal and monoclonal antibody preparation. The full-length Adhesin protein can be used or, alternatively, the invention provides antigenic peptide fragments of Adhesin for use as immunogens. The antigenic peptide of Adhesin comprises at least 8 (preferably 10, 15, 20, or 30) amino acid residues of the amino acid sequence shown in SEQ ID NO:2 and encompasses an epitope of Adhesin such that an antibody raised against the peptide forms a specific immune complex with Adhesin. Preferably, the antigenic peptide of Adhesin comprises at least 8 or more amino acids of sequences shown in SEQ ID NO: 2, 3-5, or 8-17. More preferably, the antigenic peptide of Adhesin comprises at least 8 or more amino acids of sequences shown in SEQ ID NO: 2.

Useful antibodies include antibodies which bind to a domain or subdomain of Adhesin described herein (e.g., attachment site).

An Adhesin immunogen typically is used to prepare antibodies by immunizing a suitable subject, (e.g., rabbit, goat, mouse or other mammal) with the immunogen. An appropriate immunogenic preparation may contain, for example, recombinantly expressed Adhesin protein or a chemically synthesized Adhesin polypeptide. The preparation may further include an adjuvant, such as Freund's complete or incomplete adjuvant, or similar immunostimulatory agent. Immunization of a suitable subject with an immunogenic Adhesin preparation induces a polyclonal anti-Adhesin antibody response.

Accordingly, another aspect of the invention pertains to anti-Adhesin antibodies. The term "antibody" as used herein refers to immunoglobulin molecules and immunologically active portions of immunoglobulin molecules, i.e., molecules that contain an antigen binding site which specifically binds an antigen, such as Adhesin. A molecule which specifically binds to Adhesin is a molecule which binds Adhesin, but does not substantially bind other molecules in a sample. Examples of immunologically active portions of immunoglobulin molecules include F(ab) and F(ab')2 fragments which can be generated by treating the antibody with an enzyme such as pepsin. The invention provides polyclonal and monoclonal antibodies that bind Adhesin. The term "monoclonal antibody" or "monoclonal antibody composition", as used herein, refers to a population of antibody molecules that contain only one species of an antigen binding site capable of immunoreacting with a particular epitope of Adhesin. A monoclonal antibody composition thus typically displays a single binding affinity for a particular Adhesin protein with which it immunoreacts.

Polyclonal anti-Adhesin antibodies can be prepared as described above by immunizing a suitable subject with an Adhesin immunogen. The anti-Adhesin antibody titer in the immunized subject can be monitored over time by standard techniques, such as with an enzyme linked immunosorbent assay (ELISA) using immobilized Adhesin. If desired, the antibody molecules directed against Adhesin can be isolated from the mammal (e.g., from the blood) and further purified by well-known techniques, such as protein A chromatography to obtain the IgG fraction. At an appropriate time after immunization, e.g., when the anti-Adhesin antibody titers are highest, antibody-producing cells can be obtained from the subject and used to prepare monoclonal antibodies by standard techniques, such as the hybridoma technique originally described by Kohler and Milstein (1975) Nature 256: 495-497, the human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77-96) or trioma techniques. The technology for producing monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with an Adhesin immunogen as described above, and the culture supernatants of the resulting hybridoma cells are screened to identify a hybridoma producing a monoclonal antibody that binds Adhesin.

Any of the many well known protocols used for fusing lymphocytes and immortalized cell lines can be applied for the purpose of generating an anti-Adhesin monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387-402). Moreover, the ordinarily skilled artisan will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Adhesin, e.g., using a standard ELISA assay.

Additionally, recombinant anti-Adhesin antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; and Shaw et al. (1988) J. Natl. Cancer Inst. 80:1553-1559); Morrison, (1985) Science 229:1202-1207; Oi et al. (1986) Bio/Techniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060.

An anti-Adhesin antibody (e.g., monoclonal antibody) can be used to isolate Adhesin by standard techniques, such as affinity chromatography or immunoprecipitation. An anti-Adhesin antibody can facilitate the purification of natural Adhesin from cells and of recombinantly produced Adhesin. Moreover, an anti-Adhesin antibody can be used to detect Adhesin protein (e.g., in a cellular lysate or cell supernatant) in order to evaluate the abundance and pattern of expression of the Adhesin protein. Anti-Adhesin antibodies can be used diagnostically to monitor protein levels in tissue as part of a clinical testing procedure, for example, to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials known in the art. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes LUMINOL® detecting agent; examples of bioluminescent materials include luciferase, luciferin, and aequorin, and examples of suitable radioactive material include $^{125}I$, $^{131}I$, $^{35}S$ or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, beta-interferon, nerve growth factor, platelet derived growth factor, tissue plasminogen activator; or, biological response modifiers such as, for example, lymphokines, interleukin-1 (IL-1), interleukin-2 (IL-2), interleukin-6 (IL-6), granulocyte macrophase colony stimulating factor (GM-CSF), granulocyte colony stimulating factor (G-CSF), or other growth factors. Furthermore, the conjugate may be any moiety useful in the use of the invention and include those known in the art or yet to be discovered. A skilled artisan will recognize that the conjugate used depends upon the intended use of the invention.

Techniques for conjugating such therapeutic moieties to antibodies are well known, see, e.g., Arnon et al., "Monoclonal Antibodies for Immunotargeting of Drugs in Cancer Therapy", in Monoclonal Antibodies and Cancer Therapy, Reisfeld et al. (eds.), pp. 243-56 (Alan R. Liss, Inc. 1985); Hellstrom et al., "Antibodies for Drug Delivery", in Controlled Drug Delivery (2nd Ed.), Robinson et al. (eds.), pp. 623-53 (Marcel Dekker, Inc. 1987); Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985); "Analysis, Results, and Future Prospective of The Therapeutic Use of Radiolabeled Antibody In Cancer Therapy", in Monoclonal Antibodies for Cancer Detection and Therapy, Baldwin et al. (eds.), pp. 303-16 (Academic Press 1985), and Thorpe et al., "The Preparation and Cytotoxic Properties of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

In addition, antibodies of the invention, either conjugated or not conjugated to a therapeutic moiety, can be administered together or in combination with a therapeutic moiety such as a cytotoxin, a therapeutic agent or a radioactive metal ion. The order of administration of the antibody and therapeutic moiety can vary. For example, in some embodiments, the antibody is administered concurrently (through the same or different delivery devices, e.g., syringes) with the therapeutic moiety. Alternatively, the antibody can be administered separately and prior to the therapeutic moiety. Still alternatively, the therapeutic moiety is administered separately and prior to the antibody. In many embodiments, these administration regimens will be continued for days, months or years.

E. Pharmaceutical Compositions

The Adhesin nucleic acid molecules, Adhesin proteins, Adhesin immunogens, small molecules, and anti-Adhesin antibodies (also referred to herein as "Adhesin agent") of the invention can be incorporated into pharmaceutical compositions suitable for administration. Such compositions typically comprise the nucleic acid molecule, protein, antibody, immunogen, small molecules or combinations thereof and a pharmaceutically acceptable carrier. As used herein the language "pharmaceutically acceptable carrier" is intended to include any and all solvents, dispersion media, coatings, adjuvants, stabilizing agents, diluents, preservatives, antibacterial and antifungal agents, isotonic agents, adsorption delaying agents, and combinations thereof. One particularly preferred composition includes saline, preferably phosphate buffered saline. Another particularly preferred composition includes Freund's complete adjuvant. Yet another preferred composition includes both phosphate buffered saline and Freund's complete adjuvant. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In some embodiments, the pharmaceutically acceptable carrier includes adjuvants. Suitable adjuvants are those that include surfactants, oil, mycobacterium, immunostimulators, zinc proline, detergent, modified bacterial products, other components known in the art, and any combination thereof. Adjuvants commonly known in the art include, without limitation, Freund's Complete Adjuvant, Freund's Incomplete Adjuvant, Hunter's TITERMAXd® adjuvant, Gerbu Adjuvant, and Ribi's Adjuvant. One skilled in the art will appreciate that the adjuvant chosen depends upon a variety of factors including, without limitation, the specific agent employed; the age, body weight, general health, gender, and species of the subject; the route of administration; any drug combinations; and the degree of immune response desired. Preferably, the pharmaceutically acceptable carrier includes TITERMAX® adjuvant or Freund's Complete Adjuvant. More preferably, the pharmaceutically acceptable carrier includes TITERMAX® adjuvant.

The invention includes methods for preparing pharmaceutical compositions for treating or preventing an infection of *Fusobacterium*. Such methods comprise formulating a pharmaceutically acceptable carrier with an Adhesin agent that is capable of inducing an immune response to Adhesin in the subject to be treated, inhibiting the activity of Adhesin, or combinations thereof. Such compositions can further include additional active agents. Thus, the invention further includes methods for preparing a pharmaceutical composition by formulating a pharmaceutically acceptable carrier with an Adhesin agent that is capable of inducing an immune response to Adhesin in the subject to be treated, an Adhesin agent capable of inhibiting the activity of Adhesin, additional active compounds, and combinations thereof.

The Adhesin agent used in the pharmaceutical composition may be nucleic acids, protein, immunogens, or antibodies as described herein, or a small molecule. Suitable small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled artisan. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic. Preferably, the parenteral preparation is enclosed in multiple dose vials.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® EL solubilizing agent (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. These can be prepared according to methods known to those skilled in the art, for example, as described in U.S. Pat. No. 4,522,811.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193). Preferably, the dosage is about 0.5, 1, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, or 95 mg/kg of body weight. More preferably, the dosage is about 10 to 20 mg/kg. More preferably, the dosage is about 15 mg/kg.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded.

The gene therapy vectors of the invention can be either viral or non-viral. Examples of plasmid-based, non-viral vectors are discussed in Huang et al. (1999) Nonviral Vectors for Gene Therapy (supra). A modified plasmid is one example of a non-viral gene delivery system. Peptides, proteins (including antibodies), and oligonucleotides may be stably conjugated to plasmid DNA by methods that do not interfere with the transcriptional activity of the plasmid (Zelphati et al. (2000) BioTechniques 28:304-315). The attachment of proteins and/or oligonucleotides may influence the delivery and trafficking of the plasmid and thus render it a more effective pharmaceutical composition.

II. Methods

The present invention encompasses methods of detecting, treating, and preventing fusobacterial infections in a subject. The methods may be utilized to treat a subject harboring symptoms that would benefit from Adhesin compositions or that is at risk of developing a condition that would benefit from Adhesin compositions.

A. Conditions Benefiting from Adhesin Compositions

Conditions that would benefit from Adhesin compositions, such as treatment with inhibiting antibodies, Adhesin immunogens, Adhesin antisense molecules, small molecules, or proteins, may include any symptom, condition or disease that is caused by fusobacterial infection. For instance, exemplary conditions that may benefit include liver abscess, foot rot, foot abscesses, calf diphtheria, mastitis, mertritis, necrotic lesions of the oral cavity, sore throat, pharyngitis, tonsillitis, deep neck abscesses, deep neck infections, metastatic pleuropulmonary disease, necrotizing pneumonia, empyema, renal and hepatic abscesses, osteomyelitis, meningitis paravertebral abscesses, and pustular dermatitis of hypoperfused extremities.

Also, methods of the invention may be utilized to treat a population of cells that would benefit from Adhesin compositions. Such cells include those in a subject as well as those removed from a subject for therapeutic treatment, cultured cells, those used in gene-therapy practices, and any other cell that may benefit from Adhesin compositions.

B. Methods of the Invention

The Adhesin compositions described herein, including nucleic acid molecules, proteins, antisense molecules, immunogens, and antibodies, may be used in detection assays and treatment methods (e.g., therapeutic and prophylactic) of the invention. The isolated nucleic acid molecules of the invention can be used to express Adhesin protein, to detect Adhesin, and to modulate Adhesin activity. In addition, the Adhesin proteins can be used to screen drugs, compounds, or antibodies which modulate the Adhesin activity or expression as well as to treat fusobacterial infections. In addition, the anti-Adhesin antibodies of the invention can be used to detect and isolate Adhesin proteins as well as modulate Adhesin activity. Also, Adhesin immunogens can be administered to a subject to induce an immune response in a subject to treat or prevent fusobacterial infections, such as an Adhesin vaccine. Further, Adhesin antisense molecules can be used to modulate Adhesin activity, such as inhibit Adhesin activity. This invention further pertains to novel agents identified by the above-described screening assays and uses thereof for treatments as described herein.

1. Treatment Methods

In one embodiment, the Adhesin compositions described herein may be used in methods of treating subjects infected with *Fusobacteria*. In another embodiment, the Adhesin compositions described herein may be used in methods of treating subjects not infected with *Fusobacteria*. In another embodiment, the Adhesin compositions may be used to alleviate conditions caused by, or related to *Fusobacteria* infection. Yet, in other embodiments, the Adhesin compositions may be used to decrease mortality caused by *Fusobacteria* infection.

The Adhesin compositions may be administered to a subject in a single dose or multiple doses. A dosing regimen, either single or multiple doses, may be followed with a booster dose. The amount of time a booster dose may follow a dosing regimen composition depends upon the efficacy of the dosing regimen.

In other embodiments, subjects being administered Adhesin compositions of the invention may also be administered combination therapies, in which additional treatments are used. Such additional treatments include therapeutic treatments known in the art, or yet to be discovered, that provide a benefit to the subject. For example, a subject undergoing Adhesin vaccination against fusobacterial infection may be administered therapeutics such as leukotoxin vaccine, immunomodulating agents, or antisense molecules. The additional therapeutics may be administered individually, sequentially, or in combination with other therapeutics or the Adhesin composition.

In some embodiments, the efficacy of the Adhesin agents may be measured by the effect on the agents on symptoms experienced by the recipient subject. For example, a reduction in the incidence or severity, up to and including complete prevention, of symptoms of *Fusobacterium* can be measured to assess the efficacy of the Adhesin agents. Also, the presence of *Fusobacterium* infection can be used to measure the efficacy of the Adhesin agents. Symptoms of *Fusobacterium* infection in humans include Lemiere's syndrome, postanginal sepsis, tonsillitis, septic thrombophlebitis of the internal jugular vein, septicemia, septic emboli, purulent otits, septic arthritis, cerebral abscess, cough, sore throat, oropharyngeal sepsis, cervical lymphadenopathy, high level of C-reactive protein, lung lesions, metastatic lesions, high fever, chills/rigor, and combinations thereof. Symptoms of *Fusobacterium* infection in animals include liver abscesses, foot rot, ruminal acidosis, rumenitis, thrush, reduced weight gain, reduced feed conversion efficiency, and combinations thereof. Methods of detecting and monitoring such symptoms are known in the art and contemplated herein. In one embodiment, subjects prophylactically treated with Adhesin agents to prevent *Fusobacterium* infection can be monitored for the presence of *Fusobacterium* infection and symptoms associated therewith. In one embodiment, subjects having symptoms of *Fusobacterium* infection can be monitored for alleviation of such symptoms. Preferably, there are no symptoms of *Fusobacterium* infection detected. More preferably, there is a reduction in incidence of symptoms by about 5-99% when compared to a control subject not receiving an Adhesin agent. More preferably, there is a reduction in incidence of symptoms by about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40% or more when compared to a control subject not receiving an Adhesin agent. More preferably, there is a reduction in incidence of symptoms by about 10% when compared to a control subject not receiving an Adhesin agent. In one embodiment, the reduction in incidence of symptoms is detected as to a specific subject. In another embodiment, the reduction in incidence of symptoms is detected as to a group of subjects. In another embodiment, the reduction in incidence of symptoms is detected as to a herd.

In some embodiments, the Adhesin agents can be administered to a subject to decrease mortality caused by *Fusobacterium* infection. Preferably, mortality caused by *Fusobacterium* infection is eliminated. More preferably, there is a decrease in mortality rate of about 1-99% when compared to a control subject not administered an Adhesin agent. More preferably, there is a decrease in mortality rate of about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95% or more when compared to a control subject not receiving an Adhesin agent. More preferably, there is a decrease in mortality rate of about 10% when compared to a control subject not receiving an Adhesin agent. In one embodiment, the decrease in mortality rate is detected as to a specific subject. In another embodiment, the decrease in mortality rate is detected as to a group of subjects. In another embodiment, the decrease in mortality rate is detected as to a herd.

2. Detection Methods

Another aspect of the present invention relates to diagnostic assays for detecting a fusobacterial infection, in the context of a biological sample (e.g., blood, serum, cells, tissue) to thereby determine whether a subject is infected with *Fusobacterium*. An exemplary method for detecting the presence or absence of Adhesin in a sample involves obtaining a sample from a test subject and contacting the sample with a compound or an agent capable of detecting Adhesin protein or nucleic acid (e.g., mRNA, genomic DNA) that encodes Adhesin protein such that the presence of Adhesin is detected in the sample. An agent for detecting Adhesin mRNA or genomic DNA is a labeled nucleic acid probe capable of hybridizing to Adhesin mRNA or genomic DNA. The nucleic acid probe can be, for example, a full-length Adhesin nucleic acid, such as the nucleic acid of SEQ ID NO:1, or a portion thereof, such as an oligonucleotide of at least 15, 30, 50, 100, 250, 500, 750 or more nucleotides in length and sufficient to specifically hybridize under stringent conditions to mRNA or genomic DNA. Other suitable probes for use in the diagnostic assays of the invention are described herein.

An agent for detecting Adhesin protein can be an antibody capable of binding to Adhesin protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The detection method of the invention can be used to detect Adhesin mRNA, protein, or genomic DNA in a sample in vitro as well as in vivo. For example, in vitro techniques for detection of Adhesin mRNA include Northern hybridizations and in situ hybridizations. In vitro techniques for detection of Adhesin protein include enzyme linked immunosorbent assays (ELISAs), Western blots, immunoprecipitations and immunofluorescence. In vitro techniques for detection of Adhesin genomic DNA include Southern hybridizations. Furthermore, in vivo techniques for detection of Adhesin protein include introducing into a subject a labeled anti-Adhesin antibody. For example, the antibody can be labeled with a radioactive marker whose presence and location in a subject can be detected by standard imaging techniques.

In one embodiment, the sample contains protein molecules from the test subject. Alternatively, the biological sample can contain mRNA molecules from the test subject or genomic DNA molecules from the test subject.

In another embodiment, the methods further involve obtaining a control sample from a control subject, contacting the control sample with a compound or agent capable of detecting Adhesin protein, mRNA, or genomic DNA, such that the presence of Adhesin protein, mRNA or genomic DNA is detected in the sample, and comparing the presence of Adhesin protein, mRNA or genomic DNA in the control sample with the presence of Adhesin protein, mRNA or genomic DNA in the test sample.

C. Delivery Means and Routes

Methods of administration include any method known in the art or yet to be discovered. Exemplary administration methods include intravenous, intraocular, intratracheal, intratumoral, oral, rectal, topical, intramuscular, intraarterial, intrahepatic, intrathoracic, intrathecal, intracranial, intraperitoneal, intrapancreatic, intrapulmonary, or subcutaneously. Preferably, the method of administration is intramuscular.

Adhesin compositions of the invention are typically administered to a subject in an amount sufficient to provide a benefit to the target microenvironment of the subject. This amount is defined as a "therapeutically effective amount." The therapeutically effective amount will be determined by the efficacy or potency of the particular composition, the duration or frequency of administration, and the size and condition of the subject, including that subject's particular treatment response. Additionally, the route of administration should be considered when determining the therapeutically effective amount. It is anticipated that the therapeutically effective amount of an Adhesin composition of the invention will range from about 0.1 ml/kg to about 35 ml/kg. Preferably, the therapeutically effective amount of an Adhesin composition of the invention ranges from 0.1 ml/kg to 1 ml/kg. Depending on the target area and desired therapeutic agent used in conjunction (of in certain instances no additional therapeutic agent will be used) with the Adhesin composition the amount of Adhesin composition can include 0.01%, 1%, 5%, 10%, 15%, 20%, 25%, 30%, 35%, 40%, 45%, 50%, 55%, 60%, 65%, 70%, 75%, 80%, 85%, 90%, 95%, 99%, or 100% of the total therapeutic composition. In determining the therapeutically effective amounts, one skilled in the art will also consider the existence, nature, and extent of any adverse effects that accompany the administration of a particular compound in a particular subject.

III. Kits

The present invention provides articles of manufacture and kits containing materials useful for preventing, treating, or detecting fusobacterial infection. The article of manufacture may include a container of a composition as described herein with a label. Suitable containers include, for example, bottles, vials, and test tubes. The containers may be formed from a variety of materials such as glass or plastic. The container holds a composition having an active agent which is effective for preventing, treating, or detecting fusobacterial infection. The active agent is at least one Adhesin composition of the invention and may further include additional Adhesin compositions or bioactive agents known in the art for treating the specific condition.

For antibody-based kits, the kit may comprise, for example: (1) a first antibody (e.g., attached to a solid support) which binds to Adhesin protein; and, optionally, (2) a second, different antibody which binds to Adhesin protein or the first antibody and is conjugated to a detectable agent. For oligonucleotide-based kits, the kit may comprise, for example: (1) a oligonucleotide, (e.g., a detectably labeled oligonucleotide), which hybridizes to a Adhesin nucleic acid sequence or (2) a pair of primers useful for amplifying an Adhesin nucleic acid molecule.

The kit may also comprise, a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for use. The label on the container may indicate that the composition is useful for preventing, treating, or detecting specific conditions and may also indicate directions for administration.

DEFINITIONS

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1-6.3.6. A, non-limiting example of stringent hybridization conditions are hybridization in 6× sodium chloride/sodium citrate (SSC) at about 45° C., followed by one or more washes in 0.2.×SSC, 0.1% SDS at 50-65° C. (e.g., 50° C. or 60° C. or 65° C.) Preferably, the isolated nucleic acid molecule of the invention that hybridizes under stringent conditions corresponds to a naturally-occurring nucleic acid molecule. As used herein, a "naturally-occurring" nucleic acid molecule refers to an RNA or DNA molecule having a nucleotide sequence that occurs in a human cell in nature (e.g., encodes a natural protein).

As used herein, the terms "gene" and "recombinant gene" refer to nucleic acid molecules comprising an open reading frame encoding an Adhesin protein, preferably 40 kDa Adhesin isolated from *Fusobacterium necrophorum* or variant thereof.

As used herein, the terms "protein" and "recombinant protein" refer to amino acid molecules comprising an Adhesin protein, preferably 40 kDa Adhesin isolated from *Fusobacterium necrophorum* or variant thereof.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) that which naturally flank the nucleic acid (i.e., sequences located at the 5' and 3' ends of the nucleic acid) in the genomic DNA of the organism from which the nucleic acid is derived. For example, in various embodiments, the isolated Adhesin nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 50-99% or more identity are defined herein as sufficiently identical. Preferably, the amino acid or nucleotide sequence has about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more identity. More preferably, the amino acid or nucleotide sequence has about 55, 56, 57, 58, 59, 60, 61, 62, 63, 64, 65, 66, 67, 68, 69, 70% or more identity. More preferably, the sequence has about 60% identity.

The term "sample" refers to a cell, a population of cells, biological samples, and subjects, such as mammalian subjects. The term "biological sample" refers to tissues, cells and biological fluids isolated from a subject, as well as tissues, cells and fluids present within a subject.

As used herein, "administering" is used in its broadest sense to mean contacting a subject with a composition of the invention.

As used herein, "subject" refers to a living organism having a central nervous system. In particular, subjects include, but are not limited to, human subjects or patients and companion animals. Exemplary companion animals may include domesticated mammals (e.g., dogs, cats, horses), mammals with significant commercial value (e.g., dairy cows, beef cattle, sporting animals), mammals with significant scientific values (e.g., captive or free specimens of endangered species), or mammals which otherwise have value. Suitable subjects also include: mice, rats, dogs, cats, ungulates such as cattle, swine, sheep, horses, and goats, lagomorphs such as rabbits and hares, other rodents, and primates such as monkeys, chimps, and apes. In some embodiments, subjects may be diagnosed with a *Fusobacterium* infection, may be at risk for *Fusobacterium* infection, or may be experiencing symptoms of a *Fusobacterium* infection. Subjects may be of any age including new born, adolescence, adult, middle age, or elderly.

The phrase "therapeutically effective amount" is used herein to mean an amount sufficient to increase to some beneficial degree, preferably to increase by at least about 1 to 100 percent, more preferably by at least about 5 to 95 percent, and more preferably by at least 8 percent or higher, healing or *Fusobacterium* cell death as compared to untreated controls. An "effective amount" is a pharmaceutically-effective amount that is intended to qualify the amount of an agent or compound, that when administered to a subject, will achieve the goal of healing an injury site, increasing *Fusobacterium* cell death, or otherwise benefiting the recipient environment.

As used herein, the term "vector" refers to a nucleic acid sequence designed to be propagated and or transcribed upon exposure to a cellular environment, such as a cell lysate or a whole cell. A "gene therapy vector" refers to a nucleic acid vector that also carries functional aspects for transfection into whole cells, with the intent of increasing expression of one or more genes or proteins. In each case such vectors usually contain a "vector propagation sequence" which is commonly an origin of replication recognized by the cell to permit the propagation of the vector inside the cell. A wide range of nucleic acid vectors and gene therapy vectors are familiar to those skilled in the art.

The term "Adhesin agent" refers to any molecule capable of modulating Adhesin activity, by increasing or decreasing the activity directly or indirectly. Exemplary Adhesin agents include, without limitation, a compound, drug, small molecule, peptide, immunogen, oligonucleotide, protein, antibody, and combinations thereof. Adhesin agents may be synthetic or naturally occurring. An Adhesin agent may be a molecule identified in a screening assay as described herein. Further, an Adhesin agent can be used to induce an immune response in a subject against Adhesin.

The term "Adhesin composition" refers to any composition including at least one Adhesin agent.

The term "Adhesin indicator" refers to any molecule capable of detecting the presence of Adhesin. A suitable Adhesin indicator may be a compound, drug, small molecule, peptide, immunogen, oligonucleotide, protein, antibody, and combinations thereof.

As used herein, a "pharmaceutical composition" includes a pharmacologically effective amount of a therapeutic agent of the invention and a pharmaceutically acceptable carrier. As used herein, "pharmacologically effective amount," "therapeutically effective amount" or simply "effective amount" refers to that amount of an agent effective to produce the intended pharmacological, therapeutic or preventive result. For example, if a given clinical treatment is considered effective when there is at least a 15% reduction in a measurable parameter associated with a disease or disorder, a therapeutically effective amount of an agent for the treatment of that disorder or disease is the amount necessary to effect at least a 15% reduction in that parameter.

The term "pharmaceutically acceptable carrier" is used interchangeably with "veterinary acceptable carrier" and both refer to a carrier for administration of a therapeutic agent. Such carriers include, but are not limited to, saline, buffered saline, dextrose, water, glycerol, ethanol, and combinations thereof. The term specifically excludes cell culture medium. For drugs administered orally pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and clactose, while corn starch and alginic acid are suitable disintegrating agents. Binding agents may include starch and gelatin, while the lubricating agent, if present, will generally be magnesium stearate, stearic acid or talc.

In practicing the present invention, many conventional techniques in molecular biology, microbiology, and recombinant DNA are used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins eds.); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

EXAMPLES

The following examples are simply intended to further illustrate and explain the present invention. The invention, therefore, should not be limited to any of the details in these examples.

Example 1: Materials and Methods

Bacterial strains and culturing. EJG (bovine adrenal capillary endothelial cells) and CPAE (Calf pulmonary artery endothelial cells) were seeded into a 6 well plate at a concentration of $1 \times 10^5$ cell/ml and incubated in Eagle's Minimal Essential Medium (EMEM) containing 10% heat-inactivated FBS for 48 hours to remove any effect of trypsinization on the eukaryotic surface proteins. Overnight cultures of FNN (strain 8L1) and FNF (strain B35), grown in pre-reduced, anaerobically sterilized brain-heart infusion broth (PRAS-BHI) to reach mid-log phase (Absorbance$_{600}$ of 0.6), were centrifuged to pellet cells, and then washed and resuspended in $CO_2$ bubbled EMEM medium containing heat-inactivated Fetal Bovine Serum (FBS). The endothelial cells were washed thoroughly (4 times) with sterile PBS and treated with *F. necrophorum* at multiplicity of infection of 100:1 for one hour at 37° C. in an anaerobic chamber. The cells were washed again with sterile PBS, treated briefly with trypsin-versene to loosen the cells, and neutralized using $CO_2$ bubbled EMEM containing heat-inactivated FBS. This medium was serially-diluted in PRAS-BHI and plated quickly on blood agar plate pre-incubated in the anaerobic chamber to determine the bacterial concentration.

*Fusobacterium necrophorum* clinical isolates from humans or cattle. Twenty-seven strains of *Fusobacterium necrophorum* (15 subsp. *necrophorum* and 12 subsp. *funduliforme*) were grown in PRAS-BHI broth, modified lactate broth and on blood agar plates were examined for the presence of fimbriae, flagella, or capsule.

Polyclonal antisera raised against OMPs (outer membrane proteins). Polyclonal antisera were raised in rabbits against the OMPs extracted from FNN (*Fusobacterium necrophorum* subsp. *necrophorum*) and FNF and (*Fusobacterium necrophorum* subsp. *funduliforme*)). Antibodies were purified using Vivapure protein A spin columns (Satorius Stedim Biotech, Aubagne Cedex, France).

Extraction of outer membrane proteins. The outer membrane proteins from *F. necrophorum* subsp. *necrophorum* strain 8L1 were isolated according to the method described by Osburn and Munson (1974) with slight modifications. Briefly, cultures were grown in 1 liter of PRAS-BHI broth for 12 to 14 hours. The cells were pelleted by centrifugation, resuspended in 20 ml of cold 0.75M sucrose-10 mM Tris buffer at pH 7.8 with lysozyme (2 mg/ml of cell suspension) and incubated on ice for 20 minutes. Formation of spheroplasts was achieved by diluting the suspension with two volumes of cold 1.5 mM EDTA at constant rate of delivery. The spheroplasts were lysed by ultrasonication in an ice-water bath with a 3-mm microtip at 20-W output pulse setting. The cell debris was removed by centrifugation at 1,200 g for 15 minutes at 4° C. The supernatant was then centrifuged at 65,000 rpm at 2-4° C. for 2 hours, and the supernatant was discarded. The pellet was resuspended in a small volume of cold 0.25 M sucrose-3.3 mM Tris-1 mM EDTA, pH 7.8 (STE buffer) and the volume was adjusted to that of the original sonicate suspension and the ultracentrifugation was repeated at 60-65,000 rpm at 2-4° C. for 2 hours. The pellet was resuspended in 2 ml of 20 mg/ml TRITON® X-100 detergent and 10 ml of STE buffer and incubated at room temperature for 45 minutes to dissolve the inner membrane. The suspension was further centrifuged at 37,000 rpm for 2 hours at 2-4° C. The pellet was collected in cold STE buffer and stored at −80° C. until use.

Culture of endothelial cells. Bovine adrenal gland capillary endothelial (EJG cells) cell line was used for this study. Cells were grown in EMEM medium with 10% fetal calf serum and 1% antibiotic solution of streptomycin and penicillin. The medium was changed every 3-4 days until the cells got monolayered. The cells were trypsinized when monolayered and subcultured to maintain the cell line for use in experiments.

Attachment of *Fusobacterium necrophorum* subsp. *necrophorum* to Karnovsky's fixed bovine endothelial cells. The EJG were seeded into a 6 well plate at a concentration of $1 \times 10^5$ cell/ml and incubated in EMEM medium containing 10% FBS for 48 h to remove any effect of trypsinization on the eukaryotic surface proteins. The cells were then fixed with Karnovsky's fixative for 10 minutes, followed by washing with sterile PBS for 3-4 times. Overnight cultures of *F. necrophorum* subsp. *necrophorum* (strain 8L1) grown in pre-reduced, anaerobically sterilized brain-heart infusion broth (PRAS-BHI) to reach mid-log phase (Absorbance$_{600}$ of 0.6). Then, 1 ml of mid-log phase grown bacteria were inoculated on to the fixed cells and incubated at 37° C. for 1 hour. After incubation, the cells were washed vigorously with sterile PBS for 3-4 times and the bound bacterial were observed in microscope.

Isolation of high affinity binding OMP, FncA (40 kDa Adhesin). The EJG cells were plated on 6-well plates and incubated for 48 hours to allow recovery of surface proteins (following trypsin treatment during cell culture splitting). The cells were fixed in modified Karnovsky's fixative and then incubated overnight with purified OMPs from subsp. *necrophorum* strain 8L1. After incubation, the unbound fraction was removed from the cells followed by washing of the cells with PBS twice followed by two washes each with increasing strengths of buffers: PBS containing 0.1% NP-40, modified RIPA (25 mM Tris.HCl pH 7.6, 150 mM NaCl, 1% NP-40, and 1% sodium deoxycholate) and finally the tightly bound OMP was collected by washing with SDS sample buffer (62.5 mM Tris-HCl pH 6.8, 25% Glycerol and 10% SDS). Each of the washes was concentrated to equal volume (10 times) and separated on a SDS-PAGE gel. The EJG cells not incubated with OMP served as negative control.

Protein sequencing. The purified protein in SDS-PAGE buffer was run on 4% stacking and 10% separation gel after overnight polymerization to avoid and N-terminal blockage. The protein was transferred to a PVDF membrane overnight by electroblotting, stained with coomassie blue staining followed by destaining. The stained PVDF membrane showing the purified OMP (FncA) was rinsed in distilled water for 4 hours while changing the water several times. Finally, the PVDF membrane containing the protein was dried between Whatman No. 1 filter paper and protein was excised to be sent on dry ice to sequencing facility at Iowa State University (Ames, Iowa). The N-terminal protein sequencing was carried out with 494 Procise Protein/peptide Sequencer/140C Analyzer using Edman degradation method (Edman, P et al. 1950). The identified amino acid sequence (SEQ ID NO: 2) was blasted in Pubmed database (on the internet at ncbi.nlm.nih.gov/pubmed/) and investigated for similar proteins present in other closely related bacterial species.

PCR analysis of different strains of subsp. *necrophorum*, subsp. *funduliforme* and human strains of *Fusobacterium necrophorum*. The presence of the fncA gene was investigated in different strains of subsp. *necrophorum*, subsp. *funduliforme* and human strains. DNA from different strains were isolated and subjected for PCR analysis using primers based on the DNA sequence of homologous proteins present in other closely related bacterium *Fusobacterium nucleatum*. The PCR conditions were as follows: 1 cycle 94° C. for 3 minutes followed by 35 cycles of denaturation at 94° C. for 1 minute, annealing at Tm −5° C. for 30 seconds, and extension at 72° C. (1 minute per kb of expected product).

Detection of Fibronectin on EJG cell culture. The cells were grown in 24 well plates and fixed with 10% methanol for 10 minutes followed by blocking with 2% non fat dry milk in PBST for half an hour. The cells were then incubated with DAPI and mouse anti-fibronectin antibody followed by washing and incubation with rhodamin conjugated Affinipure goat anti-mouse IgG antibody. The stained cells were visualized using immunofluorescence microscope (Nikon Eclipse TE-2000-U).

Far-western analysis of FncA with fibronectin. Bovine fibronectin (1 mg) was dissolved 1 ml of PBS (final concentration 1 μg/μl) and 250 μl was incubated with 250 μl of 10 mM EZ-Link Sulfo-NHS-LC-Biotin solution in PBS for 30 minutes at room temperature with constant shaking. The excess of biotin was neutralized by adding 500 μl of 1 M Tris-HCl and incubating for additional 15 minutes. The neutralized mixture was further washed 3-4 times with 5 ml PBS using 100 kDa filter and concentrated to a final volume of 200 μl. The biotinylated sample was then incubated with FncA protein blotted on nitrocellulose membrane for 2 hours at room temperature in PBST (PBS+0.05% TWEEN® 20 detergent) followed by washing with PBST three times for 10 minutes each. The biotinylated fibronectin bound to the purified FncA was detected using Avidin-HRP conjugate. The protein incubated only with Avidin-HRP served as control. To further avoid any suspicion of biotin directly binding to the purified FncA protein, a modified approach was taken where the fibronectin was directly incubated with the blotted FncA for 2 hours followed by incubation with mouse-Anti-Fibronectin antibody for 2 hours. After incubation, the blotted membrane was washed with PBST and incubated with anti-mouse IgG Ab conjugated with alkaline phosphatase and the color was developed using BCIP/NBT substrate.

Inhibition assay. The outer membrane proteins of subsp. *necrophorum* strain 8L1 (400 μg) was incubated in each well of karnovsky's fixed EJG cells grown on 6 well plate overnight and washed with PBS twice to remove unbound proteins followed by two washing of PBS+0.1% NP-40 so as to leave only FncA OMP bound to the fixed cells. Subsp. *necrophorum* strain 8L1 were grown to 0.6 OD in PRAS-BHI medium by reinoculating overnight grown culture and 1 ml of the medium containing the bacterium were inoculated to each well of Karnovsky's fixed EJG cells. The bacteria were incubated with fixed cells for 1 hour followed by washing with PBS vigorously for 3-4 times to remove unbound bacteria. The bound bacteria to the EJG cells were removed by quickly scraping the wells after adding 500 μl of trypsin and inactivating the trypsin with 1.5 ml of $CO_2$ bubbled EMEM medium containing 10% inactivated FBS.

A 100 μl of the extracted medium containing the bacteria was serially diluted in PRAS-BHI and plated on blood agar plate for enumeration.

Cloning, Sequencing and protein expression of FncA from subsp. *necrophorum*. pET22b+ vector was used to clone and express the fncA gene from subsp. *necrophorum* strain 8L1 DNA. The forward primer 5'-CGGGATCCA-GAAGTTATGCCTGCACC-3' (SEQ ID NO: 6) had a BamHI site and reverse primer 5'-GGTGGCGGCCGC-GAAAGTAACTTTCATACCAGC-3' (SEQ ID NO: 7) had NotI site for directional cloning. The enzymes for directional cloning were selected after digesting the initial PCR product that were amplified using primers based on homologous gene sequence as mentioned before with different digestive enzymes listed on multiple cloning site of pET22b+ vector and the enzymes that did not digest the product were considered suitable for cloning. The amplified product was cloned in pET22+ vector in-frame which contains a PeIB leader peptide in the N-terminal and a histidine tag on the C-terminal of the cloning site. PeIB leader peptide helps the cloned protein to be secreted in supernatant. The cloned vector was transformed in BL21(DE3) cells and the right clones were verified using colony PCR. A few of the clones that were positive in colony PCR were subjected for protein expression using IPTG by inducing the cells for 24 hours after inoculating the overnight grown clones in fresh LB medium and a few of those that showed protein expression, the sequence of the cloned DNA was determined by DNA sequencing. The protein sequence of the DNA cloned was deduced form the DNA sequencing result and further analyzed for its similarity with homologous proteins present in the database.

Western blot analysis of recombinantly expressed FncA with bovine serum challenged with *F. necrophorum* subsp. *necrophorum* strain 8L1. The supernatant of *E. coli* BL21 (DE3) cells expressing the recombinant FncA protein was subjected to SDS-PAGE analysis and blotted on nitrocellulose membrane. The blotted proteins were detected using serum from steers that were challenged with subsp. *necrophorum* strain 8L1 as primary antibody and goat anti-bovine IgG antibody conjugated with alkaline phosphatase as secondary antibody. The color was developed using BCIP/NBT substrate.

Bacterial Preparations. *Fusobacterium necrophorum* subsp. *necrophorum* strain 8L1 previously isolated from liver abscess of cattle (Narayanan et al., 1997) and stored at −80° C. was streaked onto blood-agar plates (Remel, Thermo Fisher Scientific, Lenexa, Kans.) in an anaerobic glove box (Forma Scientific, Marietta, Ohio; model 1024). The bacterial colonies were Gram-stained and their biochemical characteristics were determined using a RapID ANA II kit (Remel) in order to confirm the identity and purity of *F. necrophorum*. After the bacterial identity was confirmed, 10 ml pre-reduced anaerobic sterilized brain heart infusion broth (PRAS-BHI [Tan et al., 1992]; Becton-Dickinson, and Company, Franklin Lakes, N.J.) tubes were inoculated with single colonies and grown overnight at 39° C. to achieve starter cultures.

Animal Assignment. At 7 weeks of age, 54 five-week-old female CF1 mice (multipurpose mouse model for infectious disease) were purchased and sorted three per cage. Two weeks later, the mice were assigned into six groups at random (9 mice per group; Table 1). Groups 1 and 2 were assigned as no-vaccine controls (phosphate buffered saline [PBS]+TITERMAX® Classic adjuvant (adjuvant) [Stratech Scientific Ltd. Suffolk, U.K]), group 3 was assigned for vaccine candidate 1 (40 kDa adhesin+adjuvant), group 4 was assigned for vaccine candidate 2 (recombinant leukotoxin+adjuvant), group 5 was assigned for vaccine candidates 1+2, and group 6 was assigned for leukotoxoid vaccine (a formalin-treated culture supernatant of *F. necrophorum* strain A25+adjuvant).

TABLE 1

Vaccination and Challenge Protocol.

| | Group 1 | Group 2 | Group 3 | Group 4 | Group 5 | Group 6 |
|---|---|---|---|---|---|---|
| Day -14 | Arrival of 90 mice, randomization and separation into six groups | | | | | |
| Day 0 | PBS + adjuvant | PBS + adjuvant | Vaccine 1 (40 kDa adhesion + adjuvant) | Vaccine 2 (recombinant leukotoxin + adjuvant) | Vaccine 1 + 2 (40 kDa adhesion + recombinant leukotoxin) | Leukotoxoid (formalin treated A25 supernatant + adjuvant) |
| Day 14 | PBS + adjuvant | PBS + adjuvant | Vaccine 1 (40 kDa adhesion + adjuvant) | Vaccine 2 (recombinant leukotoxin + adjuvant) | Vaccine 1 + 2 (40 kDa adhesion + recombinant leukotoxin) | Leukotoxoid (formalin treated A25 supernatant + adjuvant) |
| Day 21 | PBS + adjuvant | PBS + adjuvant | Vaccine 1 (40 kDa adhesion + adjuvant) | Vaccine 2 (recombinant leukotoxin + adjuvant) | Vaccine 1 + 2 (40 kDa adhesion + recombinant leukotoxin) | Leukotoxoid (formalin treated A25 supernatant + adjuvant) |
| Day 42 | PBS only | Intraperitoneal challenge with *F. necrophorum* ($3.6 \times 10^6$) | | | | |
| Day 46 | | Euthanasia, organ harvesting, and plating | | | | |

Figure 9:

Example 2: *Fusobacterium Necrophorum* Subspecies *Necrophorum* Binds to Bovine Endothelial Cells with High Affinity To determine if host cell attachment is part of the pathologic process of *Fusobacterium necrophorum*, endothelial binding assays were conducted. In particular, the binding of FNN and FNF strains to EJG cells was analyzed. As detailed in Example 1, two endothelial cell lines, EJG and CPAE, were incubated with either FNN or FNF bacteria and analyzed for binding. The EJG cell line consistently exhibited more binding compared to the CPAE cell line, and was therefore used for further studies. Also, the FNN strain was found to bind with higher affinity to EJG cells compared to FNF (FIG. 1 and FIG. 9). Similar binding experiments were also performed using EJG cells treated with modified Karnovsky's fixative (2% paraformaldehyde and 2.5% glutaraldehyde in 0.1M cacodylate buffer pH 7.4) for 10 minutes. No significant differences were observed between fixed and unfixed cells in the ability of FNN or FNF bacteria to attach to the cells.

Figure 2A:
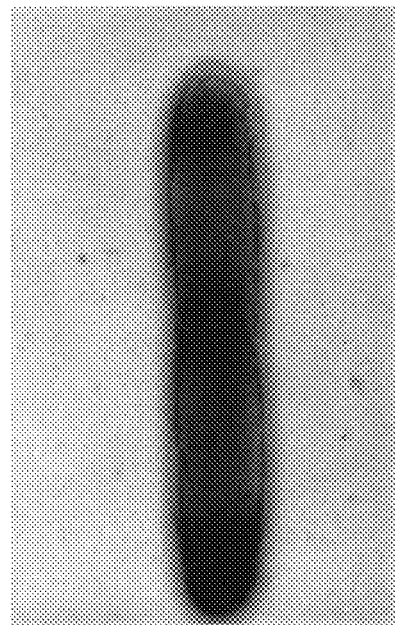
Figure 2B:
Figure 2C:
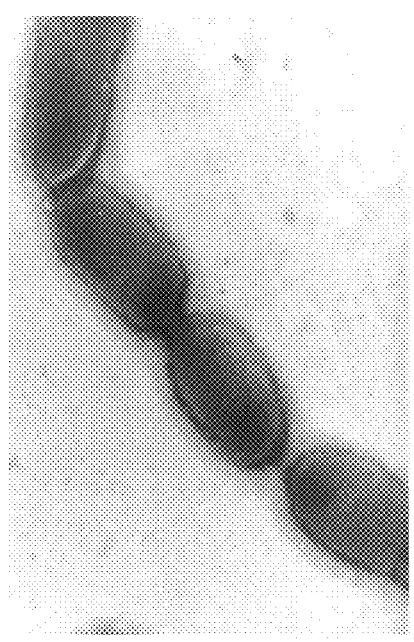
Figure 2D:
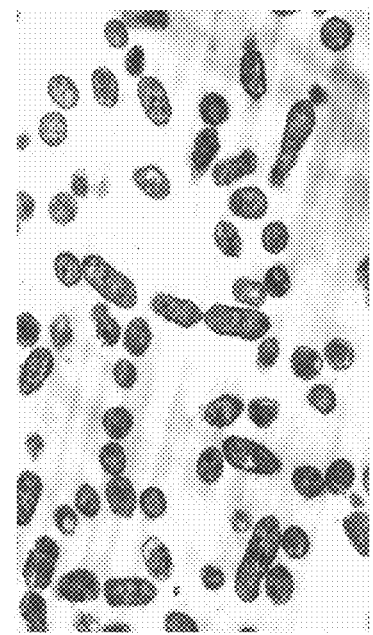

The binding of gram-negative bacteria to eukaryotic host cells may be mediated by several different mechanisms including through outermemberane capsule, fimbria, or flagella structures. To determine if the binding of FNN or FNF is mediated by these outer membrane structures, the binding of EJG was further analyzed by examining *Fusobacterium necrophorum* clinical isolates from humans or cattle. Bacterial cultures of twenty-seven strains of *Fusobacterium necrophorum* (15 subsp. *necrophorum* and 12 subsp. *funduliforme*) were delicately washed and negatively stained with 1% phosphotungstic acid. When viewed under transmission or scanning electron microscope, no fimbria, flagella or capsular structures were present in any of the bacterial cultures of the twenty-seven strains (FIGS. 2A and 2C). These results were further confirmed by transmission electron microscopy of bacterial cultures processed routinely by post fixation in 1% osmium tetraoxide and positive staining with uranyl acetate and lead citrate (FIGS. 2B and 2D). None of the twenty-seven examined strains had surface appendages such as flagella or fimbria. All *F. necrophorum* strains appeared under EM as short or long rods frequently arranged as short-chains and had typical Gram-negative cell wall structures (FIGS. 2C and 2D).

Figure 3:
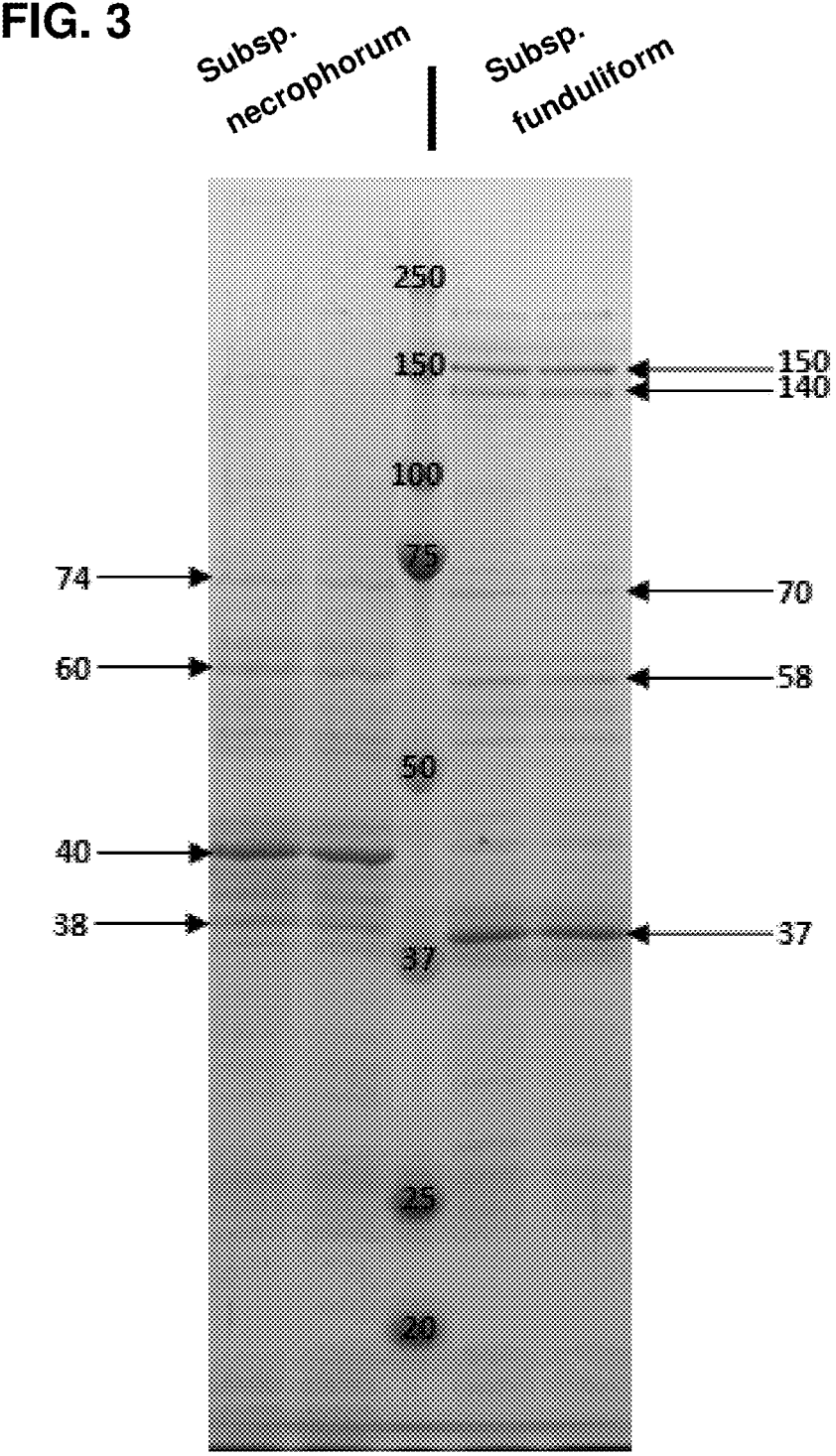

To further investigate the host cell binding, or attachment, mechanism of FNN and FNF, outer membrane proteins of each species were isolated and then compared. Specifically, the outer membrane proteins (OMPs) of FNN and FNF isolated from cattle were extracted using the method described by Osburn and Munson (1974) with slight modifications (See, Example 1 for details). Briefly, differences in OMP profiles of FNN and FNF were evaluated by SDS-PAGE and western blot analyses to identify proteins that may be related to the higher virulence of FNF. The outer membrane proteins were extracted and separated in SDS-PAGE, stained directly to visualize the bands and then transferred to nitrocellulose membrane for detection with the sera from slaughtered cattle with liver abscesses. The SDS-PAGE revealed that FNN strains had major protein bands which were absent in FNF strains. These proteins may contribute towards higher pathogenicity of FNN. As shown in FIG. 3, there were considerable differences in the OMP profiles of FNN and FNF isolated from cattle.

It was further observed that trypsin treatment of FNN reduced binding to EJG cells. Treatment of FNN for 10 minutes in EMEM containing trypsin, followed by thorough washing, significantly reduced its ability to bind to EJG cells, indicating that proteins on the surface of bacterium play an important role in binding.

Figure 4:
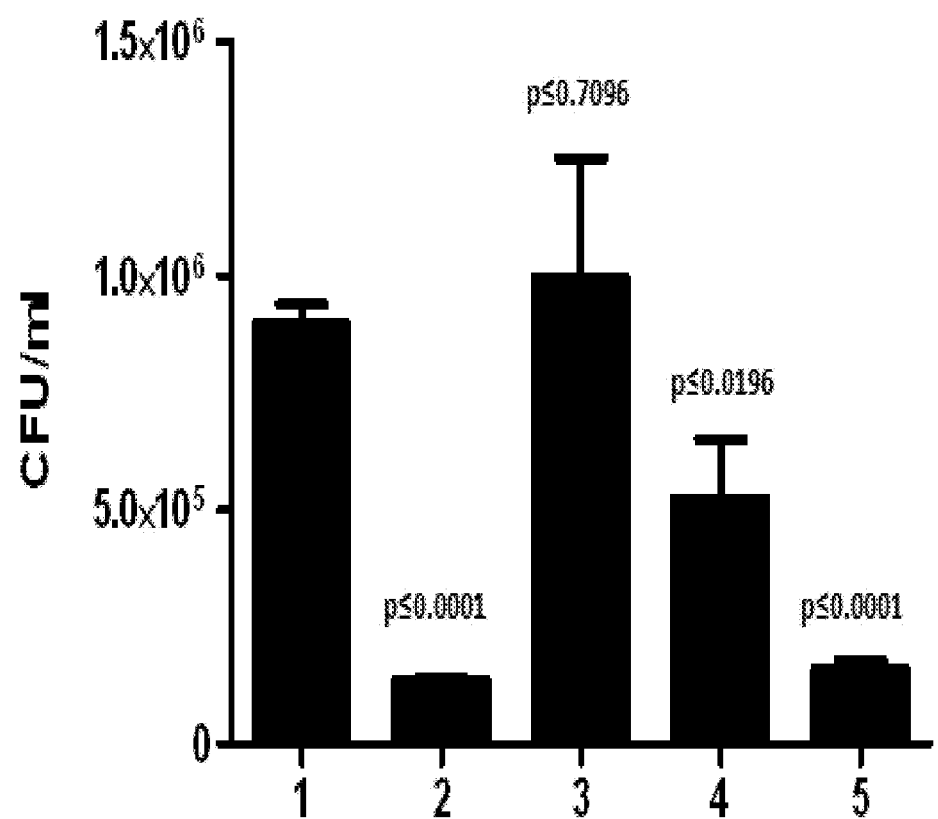

Purified OMPs and polyclonal antisera raised against OMPs reduced binding of FNN to EJG cells. Fixed EJG cells were incubated with OMP purified from FNN before performing the binding assays. There was a significant reduction in binding of FNN (FIG. 4). Polyclonal antisera were raised in rabbits against the OMPs extracted from FNN and FNF. Antibodies were purified using Vivapure protein A spin columns. FNN cultures pretreated with antiserum against OMPs of FNN reduced their binding to EJG cells, whereas the antiserum against OMPs of FNF did not have significant inhibitory effect on binding (FIG. 4). Antiserum against OMPs of FNF significantly reduced binding of FNF strains (but not FNN strains) to EJG cells. This subspecies-specific inhibition of binding suggests differences between FNF and FNN in the OMPs involved in their binding to EJG cells. The attachment of FNN to EJG cells (FIG. 4, #1), was reduced significantly when pretreated with polyclonal antisera raised against OMP of FNN (FIG. 4, #2). The attachment was not reduced when pretreated with polyclonal antisera raised against OMP of FNF (FIG. 4, #3), but was reduced significantly when EJG cells were pretreated with subsp. *necrophorum* OMPs (FIG. 4, #4) or with 40 kDa adhesin (FIG. 4, #5). FNN cultures pretreated with antiserum against OMPs of FNN reduced their binding to EJG cells, whereas the antiserum against OMPs of FNN did not have significant inhibitory effect on binding (FIG. 4). Antiserum against OMPs of FNF significantly reduced binding of FNF strains (but not FNN strains) to EJG cells. This subspecies-specific inhibition of binding suggests differences between FNF and FNN in the OMPs involved in their binding to EJG cells.

Example 3: Putative Adhesins of *Bovine F. Necrophorum* Subspecies *Necrophorum*

Figure 5:
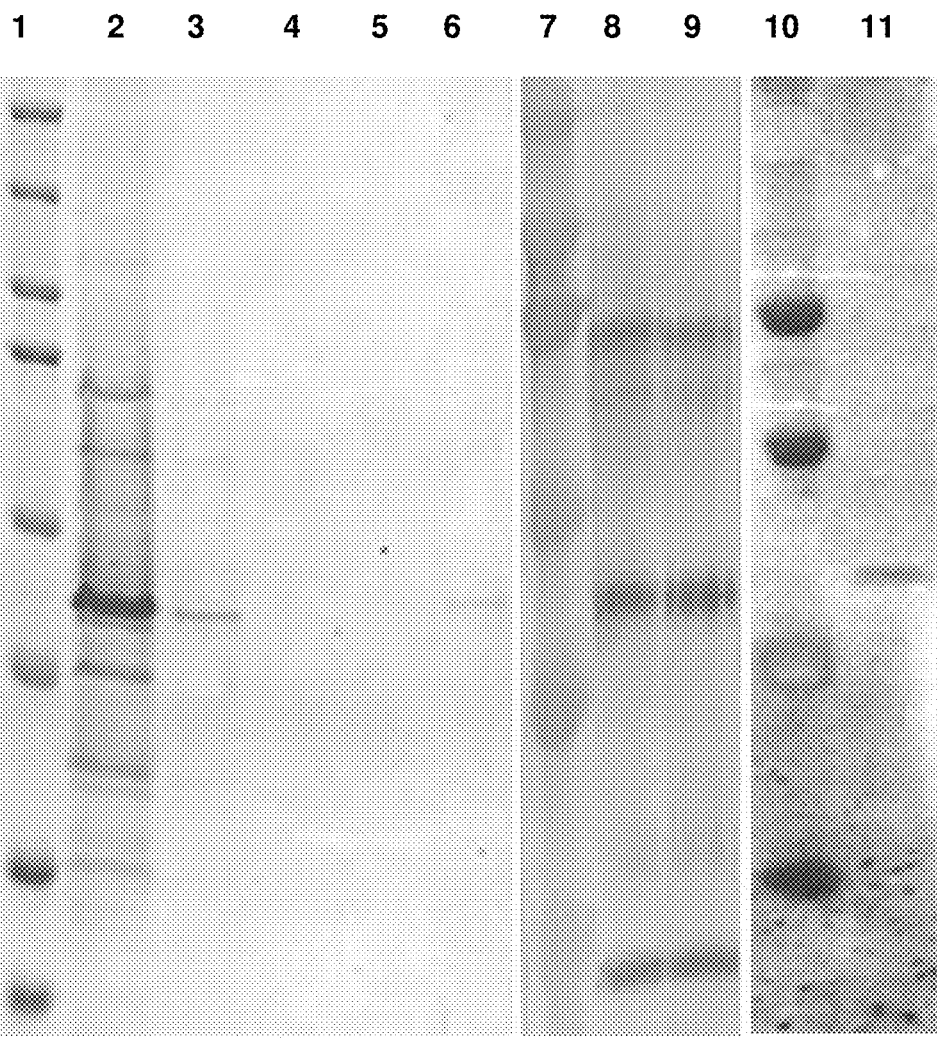
Figure 10:
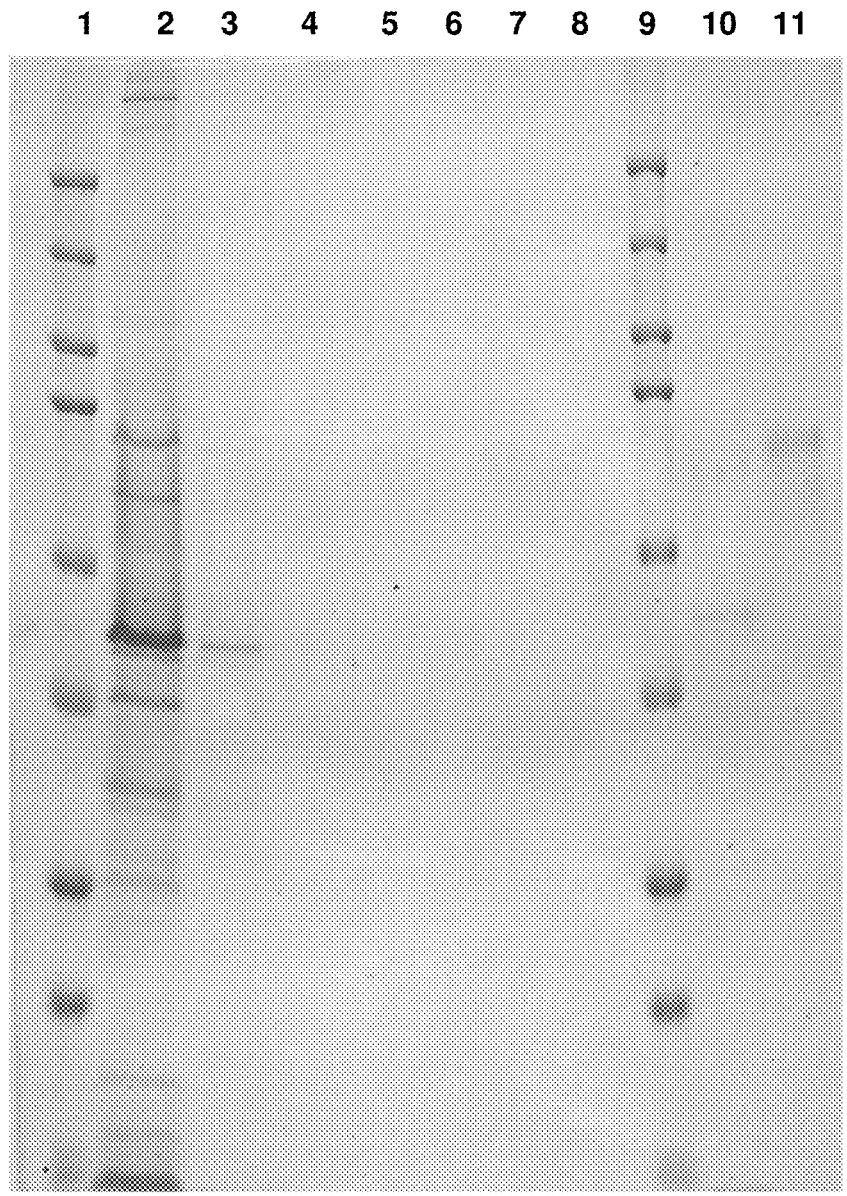

Putative adhesins of bovine FNN isolates were identified using the method in Example 1. Briefly, the EJG cells were plated on 6-well plates and incubated for 48 hours to allow recovery of surface proteins (following trypsin treatment during cell culture splitting). The cells were fixed in modified Karnovsky's fixative and then incubated overnight with purified OMPs from FNF. The cells were first washed with PBS followed by two washes each with increasing strengths of buffers: (1) PBS containing 0.1% NP-40; (2) modified RIPA (25 mM Tris.HCl pH 7.6, 150 mM NaCl, 1% NP-40, and 1% sodium deoxycholate); and, (3) final wash with SDS sample buffer (62.5 mM Tris-HCl pH 6.8, 25% Glycerol and 10% SDS). Each of the washes was concentrated 10 times and separated on a SDS-PAGE gel (FIG. 5). As shown in FIG. 10, when the OMP were incubated overnight to fixed EJG cells and the unbound fraction was removed (lane 2) followed by washing with PBS (lane 3) and detergents with increasing stringency, no protein could be detected in washing with PBS+0.1% NP-40 (lane 5 as treated cells and 6 as control cells), or modified RIPA (25 mM Tris-HCl pH 7.6, 150 mM NaCl, 1% NP-40, and 1% sodium deoxycholate) (lane 7 as treated cells and 8 as control cells). The final wash with SDS-PAGE buffer containing 10% SDS could only detach the tightly bound OMP (lane 10 as treated cells and lane 11 as control cells) which was around 40 kDa in size.

The concentrated final wash preparation revealed a 40 kDa protein in gels stained with colloidal Coomassie blue. The concentrated final wash preparation was also blotted on to a nitrocellulose membrane. Western analyses of this blot using polyclonal antisera raised against OMPs of FNN or FNF detected the 40 kDa protein and two additional proteins: sizes 70 kDa and 19 kDa proteins (FIG. 5). Far-western analysis of the blot revealed that bovine fibronectin bind with high affinity to the 40 kDa protein (FIG. 5). Briefly, for the far-western analysis, bovine fibronectin was biotinylated, and was used to hybridize the blot containing putative adhesins, and horseradish peroxidase tagged to avidin was used for detection.

The OMPs from FNF were used in a competitive binding assay to evaluate any potential role in host cell attachment the OMPs may have. It was observed that adding the purified OMPs reduced binding of FNN to EJG cells due to binding competition, which verified the function of the putative adhesins isolated. The fixed EJG cells were treated with purified OMPs. The wells were washed twice with PBS, followed by two washes in PBS+0.1% NP-40. In binding assays, there was a significant reduction in the number of FNN that attached to EJG cells, compared to EJG cells untreated with OMPs (FIG. 4, #4 and #5).

Figure 6:
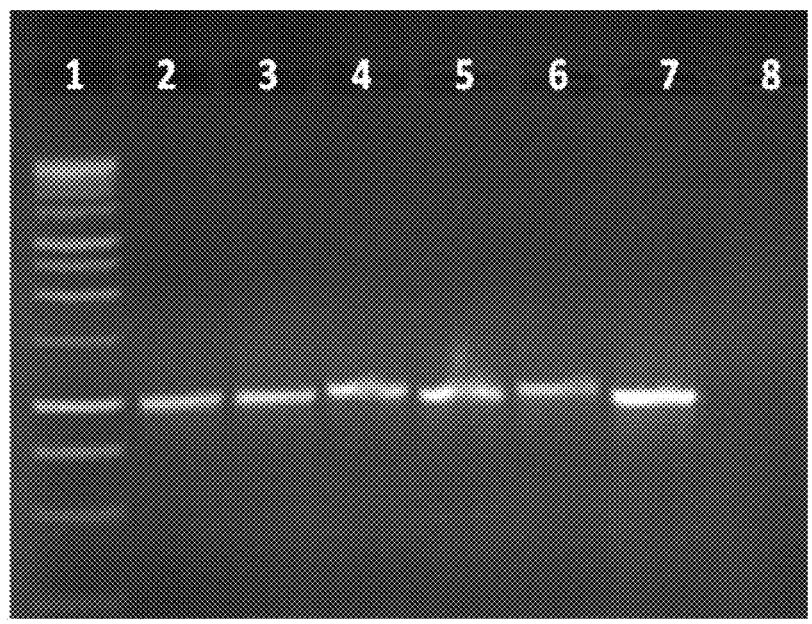
Figure 16:
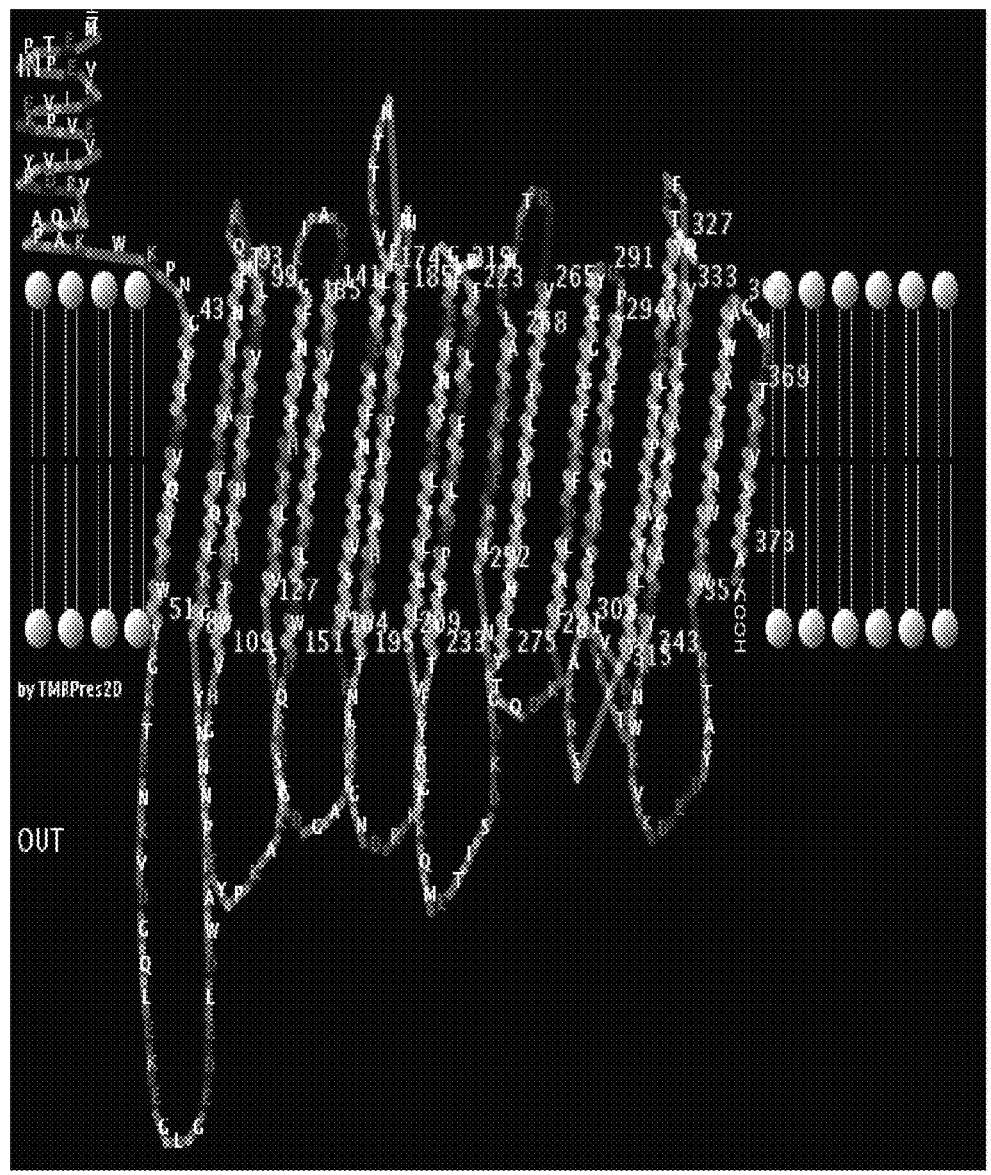
FIG. 16 shows a 2D representation of 40 kDa adhesin using Viterbi method.
Figure 17:
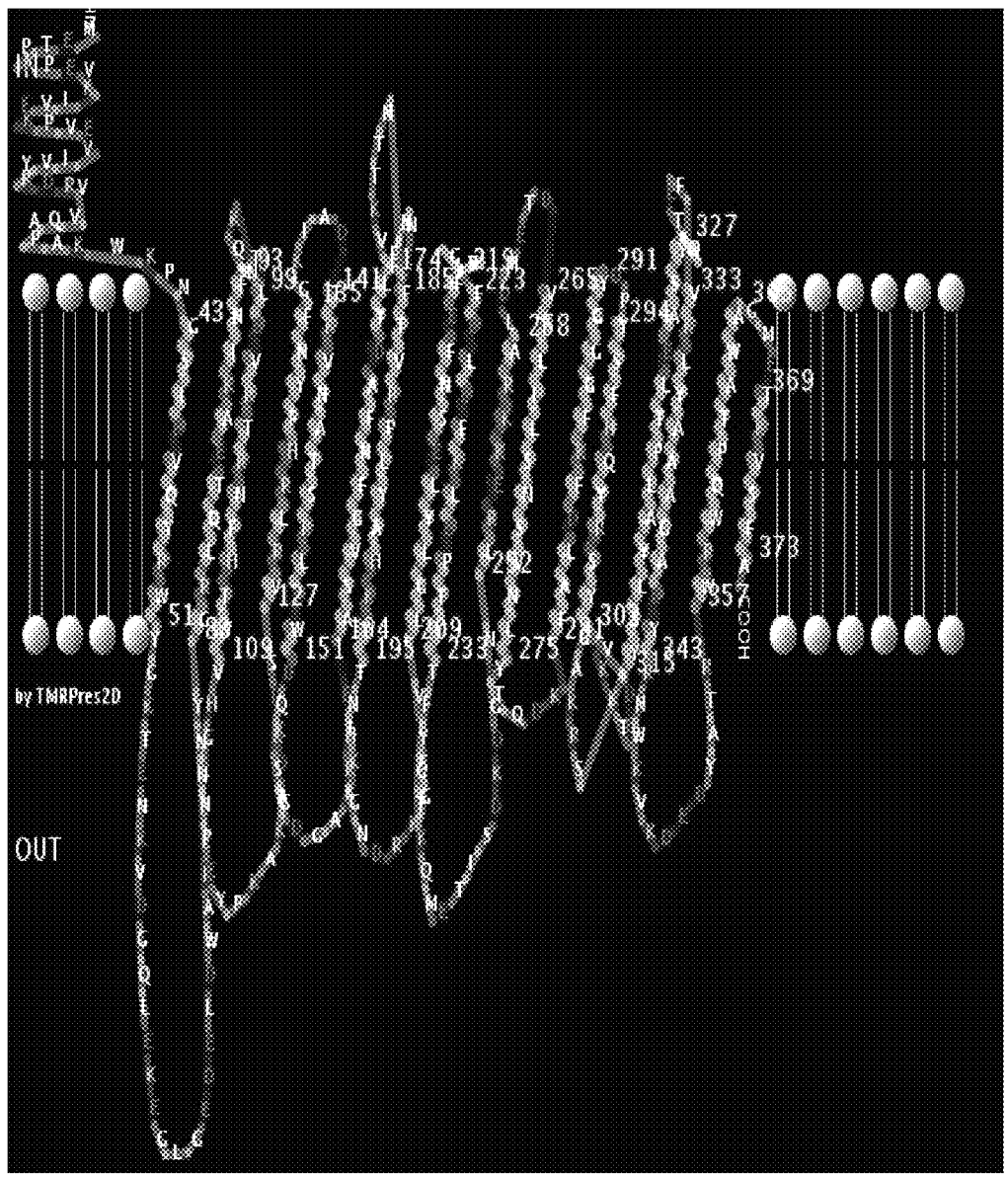
FIG. 17 shows a 2D representation of 40 kDa adhesin using N-best method.
Figure 18:
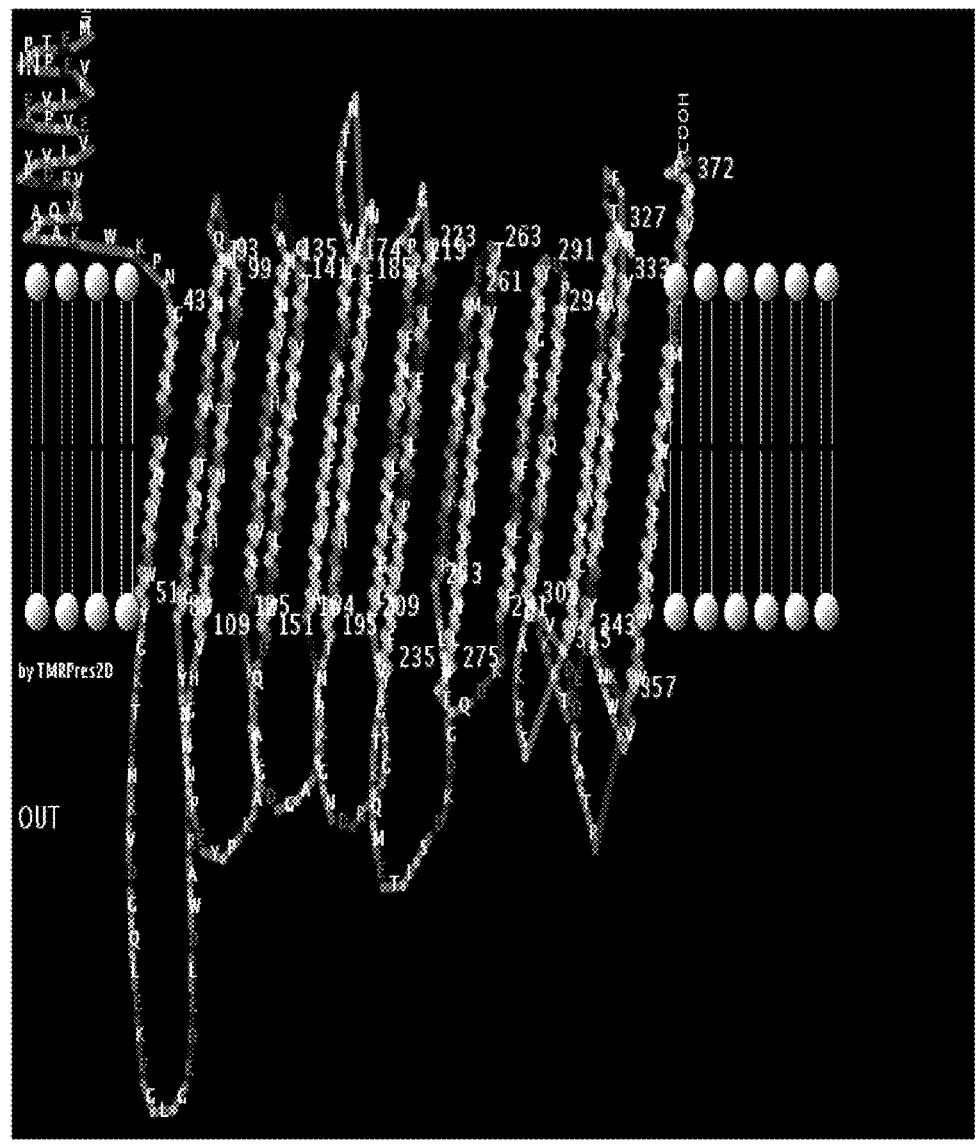
FIG. 18 shows a 2D representation of 40 kDa adhesin using a posterior decoding method.
Figure 19:
FIG. 19 shows large abscesses (white areas) in the liver of a mouse (from no-vaccine control) infected intra-peritoneally with *F. necrophorum*; and, FIG. 20 shows the isolation of *F. necrophorum* as pure cultures from the liver, lung, and spleen from a no-vaccine control mouse.

Example 4: Protein Analysis and in Vitro Expression of the Putative 40 kDa Adhesin The 40 kDa adhesin has not been shown previously to be present in *F. necrophorum* or implicated as a protein that facilitates attachment to host cell surfaces. To further characterize the 40 kDa adhesion, the 40 kDa protein was sequenced and analyzed using in vitro expression experiments. The piece of SDS-PAGE gel containing the 40 kDa protein from Example 2 was cut and submitted for protein microsequencing. The N-terminal amino acid sequence (Iowa State Univ. sequencing facility) of this protein was K-E-V-M-P-A-P-M-P-E-D/E-E (SEQ ID NO: 3, 4, and 5). Blast-P sequence analysis revealed that this protein has 96% homology to a 40 kDa OMP of *F. nucleatum* and *F. periodonticum* (FomA) and *F. varium*. Sequence analysis also revealed that the proteins in other fusobacteria have a 20-aa signal peptide that is cleaved upon its expression into the periplasm. Protein modeling shows the structural features of 40 kDa Adhesin (FIGS. 16, 17, and 18). Degenerate primers were synthesized based on the N-terminal protein sequence and the DNA sequence of *F. nucleatum* published in Genbank X72582.1. The PCR amplified a fragment of 1.25 kb with cattle isolates of subsp. *necrophorum*, and a slightly smaller 1.15 kb fragment with cattle isolates of subsp. *funduliforme* (FIG. 6). Interestingly, these primers amplified a 1.25 kb fragment when the DNA from human strains was used as templates. Nucleotide sequence analysis of the PCR products revealed that the gene encoding this 40 kDa OMP in two subspecies had only 42% homology between them and the sequence falls out of frame after 61 amino acids and encounters a stop codon after a total of 70 amino acids in F N F.

Figure 7:
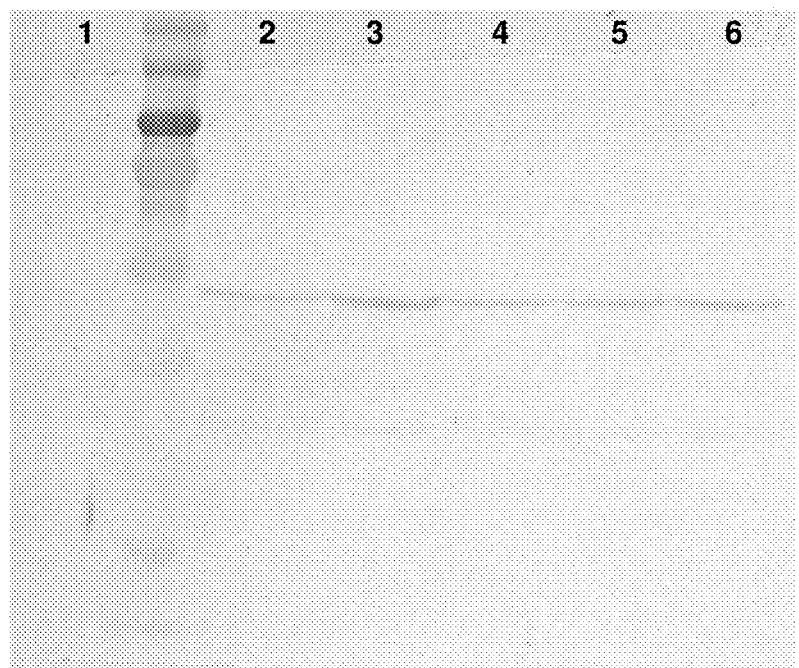

In order to clone and express the 40 kDa adhesion (SEQ ID NO: 1 and 2), primers were designed with restriction sites compatible for cloning the into pET22b+ vector, which encodes a PelB leader peptide to transport the expressed protein into periplasm of the *E. coli*. The cloned vector was transformed into *E. coli* BL21 (DE3) and induced with IPTG for expressing the proteins. A peptide of approximately 40 kDa was present in the supernatant after a six-hour induction, and this protein was detected using anti-5× histidine tag antibody, rabbit polyclonal antiserum against OMP of FNN, and serum collected from cattle experimentally challenged with FNN to induce liver abscesses (FIG. 7). This protein has also been cloned, expressed and purified in a pET45b+ vector where the protein is expressed under the control of the T7 promoter and IPTG induction leads to sequestration of the protein in *E. coli* BL21 (DE3) inclusion bodies. The protein expression was confirmed by western blot assays using antibody for the 6× histidine tag on the N-terminus of the recombinant adhesion.

Figure 11A:
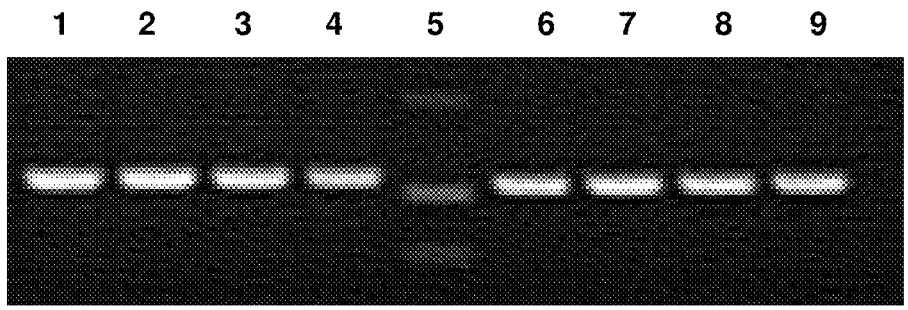
Figure 11B:
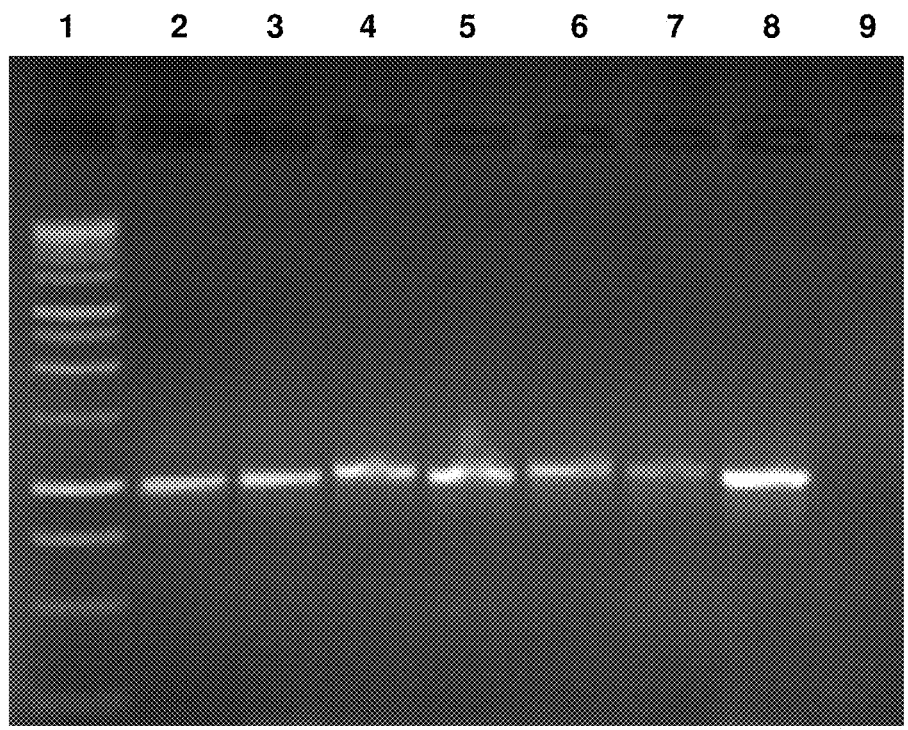

To further investigate if the identified 40 kDa adhesin is present in different strains of subsp. *necrophorum*, subsp. *funduliforme*, and human strains of *Fusobacterium necrophorum*, PCR analysis was carried out which showed that the gene is present in both subsp. *necrophorum* and subsp. *funduliforme* (FIG. 11A). PCR analysis of human strains of *F. necrophorum* also showed the presence of this gene in all the four strains tested (FIG. 11B).

Antibodies directed against 40 kDa adhesion reduced the attachment of FNN to EJG cells. The recombinanat 40 kDa protein purified by IMAC chromatography on nickel-chelation columns under denaturing conditions (with 6M urea) was used for vaccinating rabbits. FNN cultures pretreated with post-vaccination serum had significantly lower binding to EJG cells compared to the pre-vaccination serum (FIG. 16).

Figure 8:
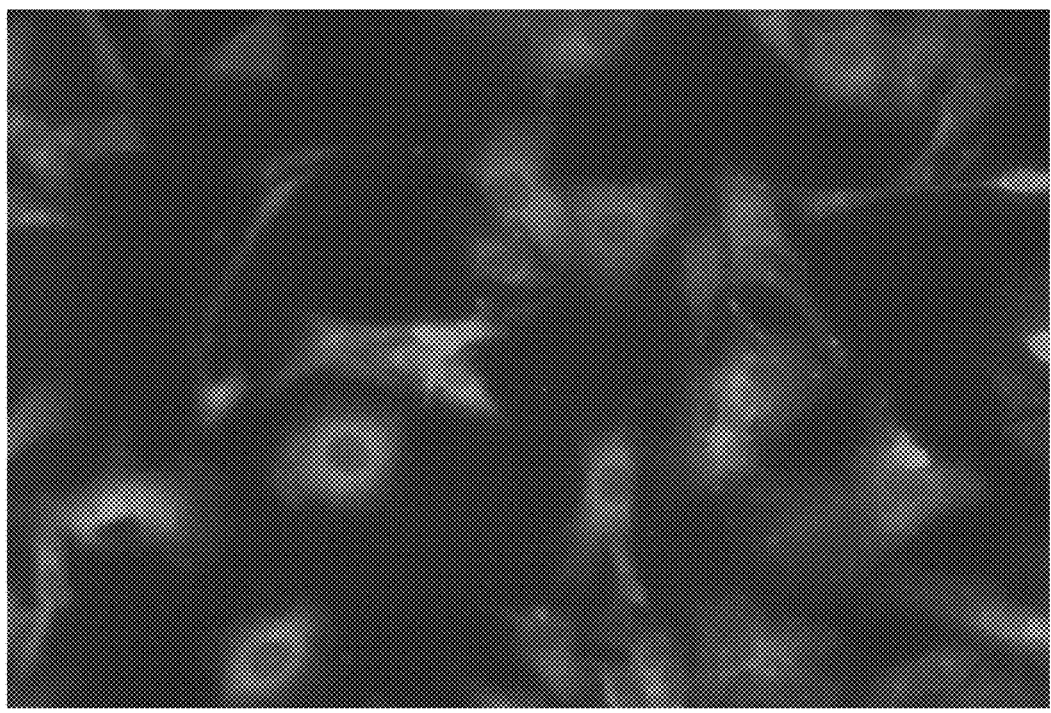

Fluorescence microscopy was applied to observe the binding activity of the 40 kDa protein and it revealed that the 40 kDa protein binds to the surface of EJG cells. The 40 kDa protein recovered from the SDS-PAGE gel was concentrated using Microcon YM-3 columns. Fixed EJG cells were incubated overnight with this protein preparation. Polyclonal antiserum against OMP of FNN was used as a primary antibody and goat anti-rabbit antibody tagged to rhodamine was used as the secondary antibody, and the cells were visualized using confocal microscopy (Nikon Eclipse TE2000-E confocal microscope). The 40 kDa protein bound tightly to the surface of EJG cells (FIG. 8). To check the specificity of the secondary antibodies, incubation with primary antibodies was omitted in negative controls.

Figure 12:
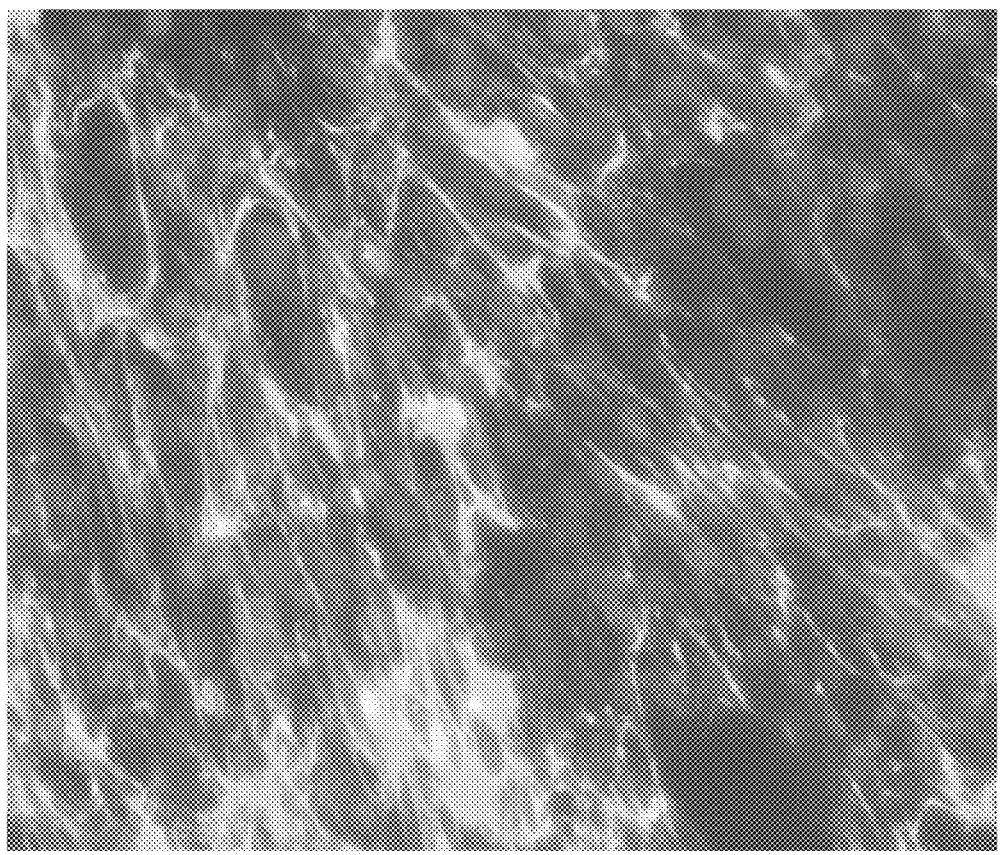
Figure 13:
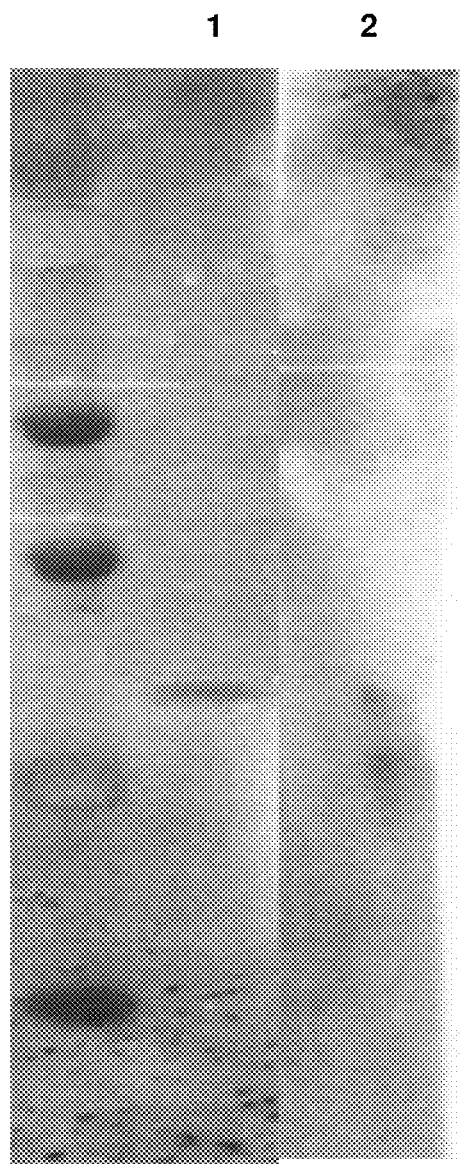
Figure 14:
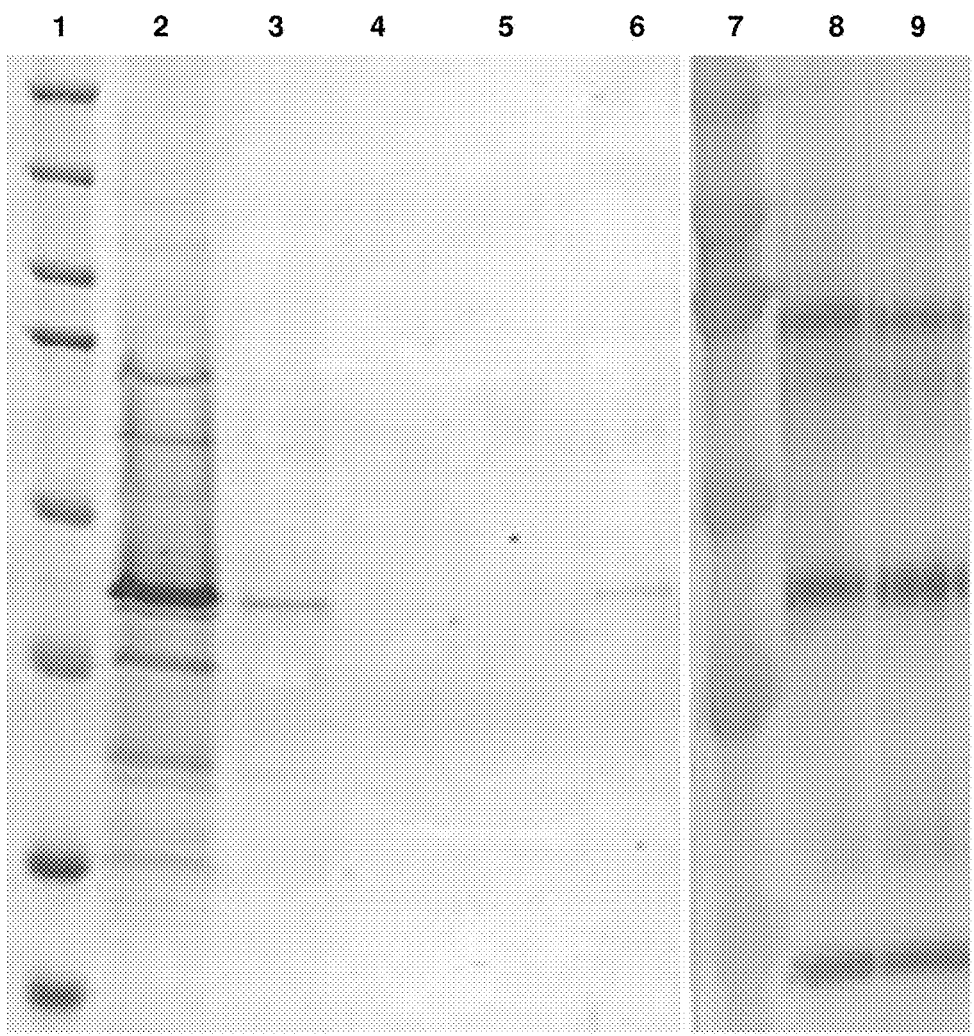
Figure 15:
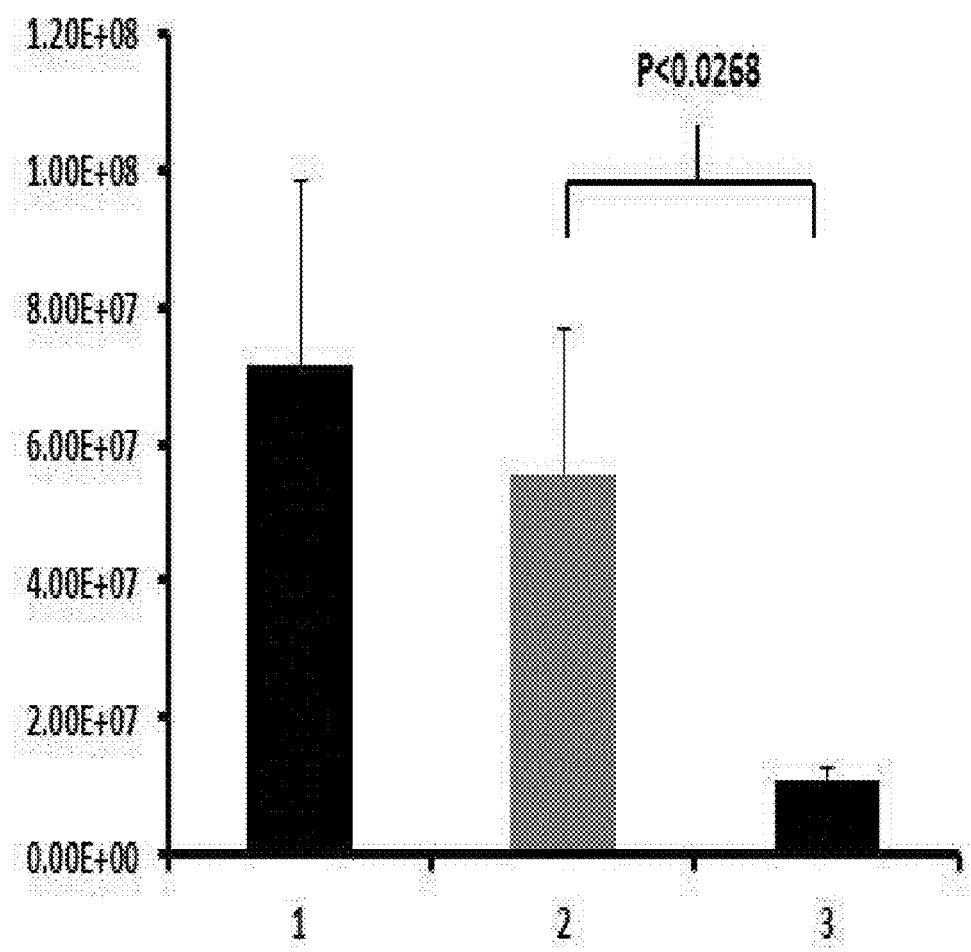

Immunohistochemistry studies showed that the EJG cells were producing fibronectin in the cell culture as shown in FIG. 12. Many outer membrane proteins of different Gram negative bacteria have been shown to bind fibronectin. The far-western analysis using biotinylated bovine fibronectin showed that the identified 40 kDa protein binds with high affinity to the fibronectin (FIG. 13). Further analysis using non-biotinylated bovine fibronectin confirmed that the binding seen in the far-western analysis is only due to actual binding of the bovine fibronectin to the identified 40 kDa protein and is not due to any excess unneutralized biotin left in the experimental step (FIG. 14).

Example 5: *Fusobacterium* Adhesin Vaccine

A vaccine was prepared using the 40 kDa Adhesin protein FncA evaluated in Example 4. The *E. coli* clones that express recombinant 40 kDa Adhesin were grown in 10 ml Luria-Bertani broth with 50 µg/ml ampicillin overnight. The following day 100 ml LB broth was inoculated with 5 ml of the overnight culture and grown to OD of 0.4 before induction with isopropylthiogalactopyranoside (IPTG). Induction time varied from 1.5 hours to 2 hours depending on the protein expression profiles. After induction, bacteria were pelleted at 5,000 rpm for 10 minutes and the proteins were purified under denaturing conditions using 6M urea. The polypeptides were dialyzed with Microcon YM-10 filters (Millipore) to exclude proteins smaller than 10 kDa. Protein concentrations were checked using Bradford method. After purification, all proteins were electrophoresed on a SDS-PAGE gel and stained with Coomassie Blue to ensure correct size of the protein. Correct protein size was also confirmed by western blot using Penta His antibodies. Immune preparations for each dose of Adhesin vaccine contained 30 µg of the FncA 40 kDa protein mixed with TITERMAX® Classic adjuvant (adjuvant) (Stratech Scientific Ltd.).

Example 6: *Fusobacterium* Leukotoxin and Recombinant Leukotoxin Vaccine

The *E. coli* clones that express recombinant leukotoxin were grown in 10 ml Luria-Bertani broth with 50 µg/ml ampicillin overnight. The following day 100 ml LB broth was inoculated with 5 ml of the overnight culture and grown to OD of 0.4 before induction with isopropylthiogalactopyranoside (IPTG). Induction time varied from 1.5 hours to 2 hours depending on the protein expression profiles. After induction, bacteria were pelleted at 5,000 rpm for 10 minutes and the proteins were purified under denaturing conditions using 6M urea. The polypeptides were dialyzed with Microcon YM-10 filters (Millipore) to exclude proteins smaller than 10 kDa. Protein concentrations were checked using Bradford method. After purification, all proteins were electrophoresed on a SDS-PAGE gel and stained with Coomassie Blue to ensure correct size of the protein. Correct protein size was also confirmed by western blot using Penta His antibodies. Immune preparations for each dose of recombinant leukotoxin vaccine contained 30 μg of recombinant leukotoxin protein mixed with TITERMAX® Classic adjuvant (adjuvant) (Stratech Scientific Ltd.). The no-vaccine controls received PBS mixed with the adjuvant. The leukotoxoid vaccine for group 6 was prepared by streaking frozen *F. necrophorum* subsp. *necrophorum* strain A25 strain on blood-agar plates. Following growth, individual colonies were inoculated in RAS-BHI broth and grown overnight. Overnight starter cultures were then used to inoculate fresh PRAS-BHI broth and incubated to reach an OD600 of 0.7 (approximately 7 hours). The bacteria were pelleted, and the supernatant was treated with polymyxin B sulfate (50 μg/ml)+0.3% formalin. All vaccines were administered via intramuscular injection into the quadriceps muscle of mice on days 0, 14, and 21.

Example 7: Analysis of *Fusobacterium Necrophorum* 40 kDa Adhesin Vaccine and Leukotoxin Vaccines Vaccine for inducing an immune response in a subject to 40 kDa Adhesin (40 kDa Adhesin Vaccine) was prepared as described in Example 5. To evaluate the efficacy of the 40 kDa Adhesin vaccine, CF1 mice were challenged with *F. necrophorum* after receiving a vaccination of 40 kDa Adhesin vaccine, leukotoxin vaccine, or sterile PBS (as a control). The mice were assigned into six groups at random (9 mice per group; Table 1). Groups 1 and 2 were assigned as no-vaccine controls (PBS+adjuvant), group 3 was assigned for 40 kDa adhesion+adjuvant vaccine, group 4 was assigned for recombinant leukotoxin+adjuvant vaccine, group 5 was assigned for 40 kDa+recombinant leukotoxin+adjuvant vaccine, group 6 was assigned for leukotoxoid vaccine (formalin-treated culture supernatant of *F. necrophorum* strain A25+adjuvant).

Blood samples were collected in 1.7 ml micro-centrifuge tubes containing heparin sodium salt, on days 0, 14, 21, 42 and 46 from the submandibular vein using goldenrod animal lancets. The volume of blood collected accounted for less than 1% of the total weight of the mouse. Plasma was extracted from the blood samples by centrifuging the blood samples at 4,000 rpm for 10 minutes, and was stored at −20° C. until further analysis. Western-blot analyses with serial dilutions of plasma were performed to determine antibody titers against specific antigens (adhesin and leukotoxin). Total outer membrane proteins of *F. necrophorum* subsp. *necrophorum* strain 8L1 were purified using standard protocols and were used in western-blots to determine the anti-adhesin titers. Culture supernatant of *F. necrophorum* subsp. *necrophorum* strain A25 (OD600=0.7) was concentrated 80-fold and used as antigen in western-blots to test antileukotoxin antibody titers. Plasma dilutions of 1:200, 1:1000, 1:5000, 1:10,000, and 1:20,000 were made in blocking buffer (2% blocking-grade non-fat dry milk in phosphate buffered saline with 0.05% TWEEN® 20 detergent [PBST]). The dilutions were loaded onto the mini-protean II multi-screen device for 4-10 hours on a rocker at 4° C. The blots were then washed three times with PBST. After washing, 10 ml of blocking buffer containing 5 μl Anti-Mouse IgG produced in goat and conjugated with alkaline phosphatase was added to the blot and rocked for 1.5 hours at room temperature. The blots were then washed with PBST and developed with BCIP/NBT premixed solution.

On day 42, groups 2 through 6 were challenged by intraperitoneal injection with *F. necrophorum* strain 8L1. The inoculum was prepared as follows: fresh pre-warmed PRAS-BHI broth tubes were inoculated with 300 μl or 600 μl of the overnight starter culture and grown to OD600 of 0.7. The resultant culture was diluted twenty times in PRAS-BHI broth and each mouse in groups 2 through 6 received a 400 ul intra-peritoneally ($3.6 \times 10^6$ total bacteria).

After the challenge, the mice were monitored every 4 hours during the light cycle to observe signs of clinical illness. Clinical signs of illness include ruffled coat, dehydration, and lethargy. The morbidity was scored based on the following criteria (0=no clinical symptoms, 1=mild ruffled coat, 2=ruffled coat, 3=ruffled coat+lethargy, 4=severe dehydration/lethargy/severe ruffled coat, and 5=no response to external stimuli).

All mice were euthanized on day 46. Organs collected at harvesting included liver, heart, lung, spleen, and brain. The liver, lungs, and spleen were each homogenized in 9 times the volume of modified lactate broth for most probable number analysis. Ten-fold serial dilutions 10-1 through 10-8 in modified lactate medium were attained using 96 well plates. The homogenated samples were also streaked on blood agar plates and incubated both anaerobically and aerobically to test for any other bacteria that may be present in the samples. Gram-staining and RapID Ana II test were also performed on each sample to confirm the identity of *F. necrophorum*. Brain, heart, and sections of lung, liver, and spleen were stored in 10% formalin for further microscopic analysis.

Serum antibody titers were analyzed using Graphpad Prism 5.03. The antibody titers, morbidity, liver abscess formation, and isolation of *F. necrophorum* were evaluated. Any probability (P) values <0.05 were considered significant. Repeated measures ANOVA test was performed and the post test data was analyzed by Tukey multiple comparison tests. Data was also run through a Friedman test with the post data analyses in Dunn's multiple comparison tests.

Immunogenicity of vaccine preparations Mice in group three (40 kDa adhesin) exhibited significant rise in antibody titers (average 4444; Table 2) against *F. necrophorum* 8L1 adhesin by day 21 when compared to day 0 ($P<0.001$), and to mice in group one (no vaccine no infection; $P<0.001$). Mice in group six (leukotoxoid vaccine) showed significant antibody production against *F. necrophorum* A25 supernatant leukotoxin by day 46 compared to day 0 ($P<0.05$), and to mice in group one ($P<0.0197$).

TABLE 2

Antibody titer values against native adhesion (Western blot).

| Treatment Groups | Day 0 | Day 13 | Day 21 | Day 42 | Day 46 (necropsy) |
|---|---|---|---|---|---|
| No Vaccine (PBS) and No Challenge | $0^a$ | $0^a$ | $0^a$ | $0^a$ | $0^a$ |
| No Vaccine (PBS) and Challenge | $0^a$ | $0^a$ | $0^a$ | $0^a$ | $0^a$ |
| 40 kDa Adhesin and Challenge | $0^a$ | $0^a$ | $4444.4^{b*}$ | $5000^{b*}$ | $20,000^{b**}$ |
| Recombinant Leukotoxin and Challenge | $0^a$ | $0^a$ | $1000^a$ | $1000^a$ | $1000^a$ |
| 40 kDa Adhesin + Recombinant Leukotoxin and Challenge | $0^a$ | $0^a$ | $1444.4^a$ | $1777.7^b$ | $2555.5^b$ |
| Leukotoxoid (culture supernatant) and Challenge | $0^a$ | $0^a$ | $0^a$ | $0^a$ | $0^a$ |

Within a row, mean titers that do not have the same superscript letters differ significantly ($P < 0.05$).
*$P < 0.05$ (different from the PBS control group).
**$P < 0.001$ (different from the PBS control group).

The 40 kDa vaccine was highly immunogenic and was better at inducing antibodies than the leukotoxoid vaccine, for example, in group 6 (leukotoxoid vaccine) the anti-leukotoxin antibody titer was 500 on day 46 compared to an anti-40 kDa adhesin antibody titer of 20,000 on day 46 in mice belonging to group 3 (40 kDa adhesin). Also, the 40 kDa vaccine elicited a quicker significant antibody response against adhesin by day 21 (just after one booster dose) compared to the leukotoxoid vaccine which had a significant antibody response to leukotoxin only by day 46 (after two boosters; Table 3).

TABLE 3

Antibody titer against leukotoxin.

| Titer values (9 in each group) | Day 0 | Day 14 | Day 21 | Day 42 | Day 46 (necropsy) |
|---|---|---|---|---|---|
| No Vaccine (PBS) and No Challenge | $0^a$ | $0^a$ | $0^a$ | $0^a$ | $0^a$ |
| No Vaccine (PBS) and Challenge | $0^a$ | $0^a$ | $0^a$ | $0^a$ | $0^a$ |
| 40 kDa Adhesin and Challenge | $0^a$ | $0^a$ | $0^a$ | $0^a$ | $0^a$ |
| Recombinant Leukotoxin and Challenge | $0^a$ | $0^a$ | $0^a$ | $0^a$ | $0^a$ |
| 40 kDa Adhesin + Recombinant Leukotoxin and Challenge | $0^a$ | $0^a$ | $0^a$ | $0^a$ | $0^a$ |
| Leukotoxoid (culture supernatant) and Challenge | $0^a$ | $0^a$ | $0^a$ | $188.8^a$ | $400^{b*}$ |

Within a row, mean titers that do not have the same superscript letters differ significantly ($P < 0.05$).
*$P < 0.05$ (different from the PBS control group).

Over the period of observation (all five days post-infection), mice in group two (no vaccine control) had a significantly higher average morbidity score (2.33, $P<0.05$). Mice in other bacterial challenged groups did not have any significant differences in morbidity rates (Table 4).

TABLE 4

Average morbidity scores of animals on Day 5 post challenge.

| Treatment Groups | Average Morbidity Score |
|---|---|
| 1 (No Vaccine [PBS] and No Challenge) | 0 |
| 2 (No Vaccine [PBS] and Challenge) | 2.33* |
| 3 (40 kDa Adhesin and Challenge) | 1.33 |
| 4 (Recombinant Leukotoxin and Challenge) | 1.78 |
| 5 (40 kDA Adhesin + Recombinant Leukotoxin and Challenge) | 1.78 |
| 6 (Leukotoxoid (culture supernatant) and Challenge) | 1.78 |

Scoring criteria: 0 = no clinical symptoms, 1 = mild ruffled coat, 2 = ruffled coat, 3 = ruffled coat + lethargic, 4 = severe dehydration/lethargy/severe ruffled coat, and 5 = no response to external stimuli;
*$P < 0.05$ (different from the PBS control group).

In group two (no-vaccine control), five of the nine mice had liver abscesses (FIG. 1; Table 5). In groups three (40 kDa adhesin vaccine) and five (40 kDa adhesin+recombinant leukotoxin) one of the nine mice per group had liver abscesses (both had a p value of 0.0665 compared to group 2). Group six (leukotoxoid) and group four (recombinant leukotoxin) had the highest incidence of liver abscess, occurring in three out of nine mice per group. Group one (no vaccine, no infection control), as expected, had no cases of liver abscess.

TABLE 5

Challenge Study: Liver abscess formation, isolation of F. necrophorum from liver, and isolation of F. ncrophorum from liver, lung, and spleen (systemic infection).

| Group | Liver abscess formation (total of nine mice per group) | Isolation of F. necrophorum from liver (total of nine mice per group) | Systemic infection with F. necrophorum (total of nine mice per group) |
|---|---|---|---|
| 1 (No Vaccine, No Infection Control) | 0 | 0 | 0 |
| 2 (No Vaccine Control) | 5[a] | 5[a] | 5[a] |
| 3 (40 kDa Adhesin Vaccine) | 1[a]* | 4[a] | 3[a] |
| 4 (Recombinant Leukotoxin Vaccine) | 3[a] | 4[a] | 3[a] |
| 5 (40 kDA Adhesin + Recombinant Leukotoxin Vaccine) | 1[a]* | 3[a] | 2[a] |
| 6 (Leukotoxoid Vaccine) | 3[a] | 4[a] | 3[a] |

Within each column, means that have the same superscript letters are not significantly different ($P < 0.05$);
*P value of 0.0665 compared to group two.

In group two (no-vaccine control), F. necrophorum was isolated from the liver in five out of nine mice. In groups three (40 kDa adhesin vaccine), four (recombinant leukotoxin vaccine), and six (leukotoxoid vaccine), F. necrophorum was isolated from the liver in four out of nine mice in each group. Of the nine mice in group five (40 kDa adhesin+ recombinant leukotoxin vaccine) F. necrophorum was isolated from the liver of three mice (Table 5). There was a significant correlation between livers carrying F. necrophorum and the presence of liver abscesses ($p<0.01$). As expected, F. necrophorum was not isolated from any mouse from group one (no vaccine, no infection control).

Figure 20:
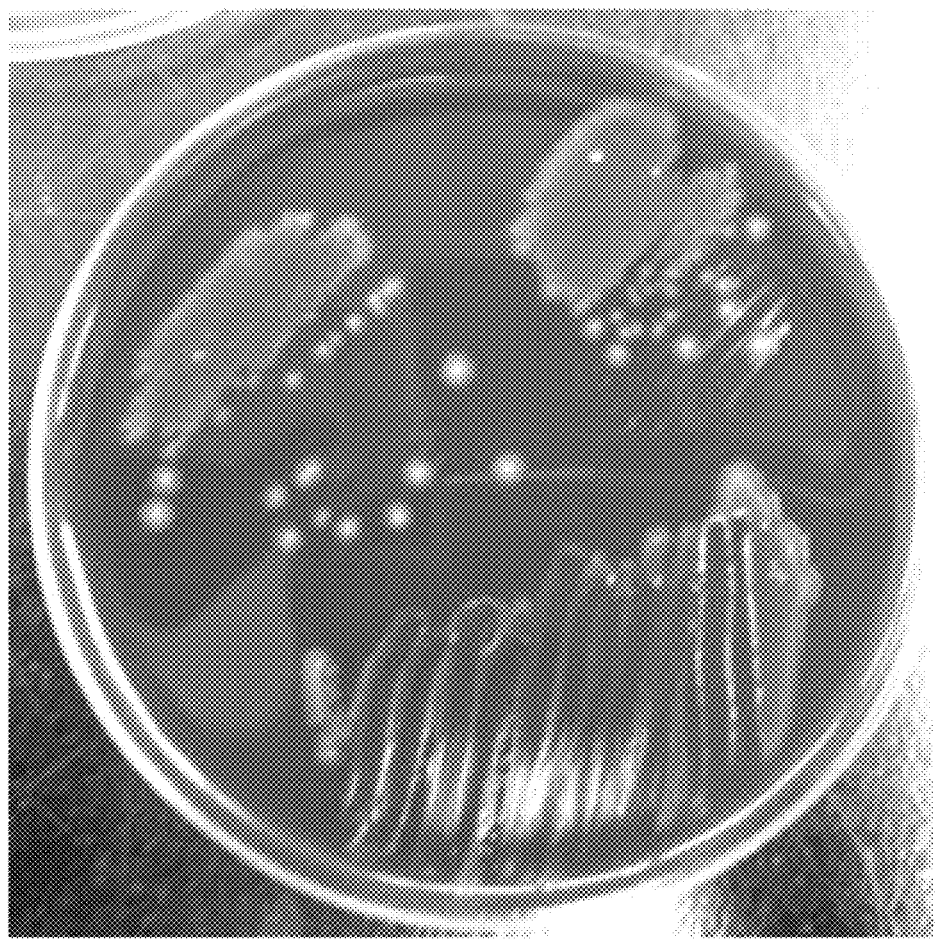

Mice were considered to carry systemic infection if F. necrophorum was isolated from the liver, lung, and spleen on anaerobic plates (divided into three sections; FIG. 20). Group one (no vaccine, no infection control) had no cases of systemic infection. Group two (no-vaccine control) had the highest rate of F. necrophorum systemic infection, occurring in five out of nine mice. Group five (40 kDa adhesin+ recombinant leukotoxin vaccine) had the lowest (two) cases of systemic infection. Groups three (40 kDa adhesin vaccine), four (recombinant leukotoxin vaccine), and six (leukotoxoid vaccine) each had three cases of systemic infection (Table 5).

In summary, these results show that the recombinant 40 kDa adhesin is immunogenic and immunoprotective, and serves as an effective vaccine to prevent or control hepatic abscesses in subjects. Only two vaccinations (one initial dose and one booster dose) with the recombinant 40 kDa adhesin induced significant specific antibody response in mice. The groups that were vaccinated with recombinant 40 kDa adhesin by itself (group three) or in combination with recombinant leukotoxin (group 5) had the lowest incidences of liver abscesses (one out of nine mice per group) compared to the no-vaccine control group. Fewer mice in groups three and five had systemic infection with F. necrophorum on five-day post-infection compared to the no-vaccine control group. F. necrophorum was re-isolated from the liver of fewer mice in groups three and five compared to the no-vaccine control group. Also, Mice in group three [40 kDa adhesin] exhibited lower incidence of liver abscesses, lesser morbidity, and a quicker antibody response than group six (leukotoxoid vaccine).

The invention illustratively disclosed herein suitably may be practiced in the absence of any element, which is not specifically disclosed herein. It is apparent to those skilled in the art, however, that many changes, variations, modifications, other uses, and applications to the method are possible, and also changes, variations, modifications, other uses, and applications which do not depart from the spirit and scope of the invention are deemed to be covered by the invention, which is limited only by the claims which follow.

What is claimed is:

1. An immunogenic composition comprising:
   a. an isolated *Fusobacterium necrophorum* peptide having a sequence selected from the group consisting of SEQ ID No. 9, SEQ ID No. 12, and SEQ ID No. 15; and,
   b. a pharmaceutically acceptable carrier comprising a component selected from the group consisting of adjuvants, stabilizing agents, preservatives, antibacterial agents, antifungal agents, adsorption delaying agents, and any combination thereof.

2. The immunogenic composition of claim 1, wherein the adjuvant is selected from the group consisting of surfactants, oil, mycobacterium, immunostimulators, zinc proline, detergent, modified bacterial products, Freund's Complete Adjuvant, Freund's Incomplete Adjuvant, Gerbu Adjuvant, Ribi's Adjuvant, and any combination thereof.

3. The immunogenic composition of claim 1, wherein the isolated *Fusobacterium necrophorum* peptide is recombinantly produced or chemically synthesized.

4. The immunogenic composition of claim 1, wherein the *Fusobacterium necrophorum* peptide induces an immune response specific for a *Fusobacterium* species when administered to an animal.

5. The immunogenic composition of claim 1 further comprising a leukotoxin immunogen.

6. The immunogenic composition of claim 1 further comprising a non-adhesin polypeptide operatively linked to the isolated adhesin protein.

7. The immunogenic composition of claim 6, wherein the non-adhesin polypeptide is the glutathione S-transferase (GST) fusion protein.

8. An immunogenic composition comprising:
   a. a *Fusobacterium necrophorum* peptide having a sequence selected from the group consisting of SEQ ID No. 9, SEQ ID No. 12, and SEQ ID No. 15; and,
   b. a pharmaceutically acceptable carrier comprising a component selected from the group consisting of adjuvants, stabilizing agents, preservatives, antibacterial agents, antifungal agents, adsorption delaying agents, and any combination thereof.

9. The immunogenic composition of claim 8, wherein the adjuvant is selected from the group consisting of surfactants, oil, mycobacterium, immunostimulators, zinc proline, detergent, modified bacterial products, Freund's Complete Adjuvant, Freund's Incomplete Adjuvant, Gerbu Adjuvant, Ribi's Adjuvant, and any combination thereof.

10. The immunogenic composition of claim 8 further comprising a leukotoxin immunogen, or a non-adhesin polypeptide operatively linked to the *Fusobacterium necrophorum* peptide.

11. A kit comprising:
   a. a *Fusobacterium necrophorum* peptide having a sequence selected from the group consisting of SEQ ID No. 9, SEQ ID No. 12, and SEQ ID No. 15;
   b. a pharmaceutically acceptable carrier comprising a component selected from the group consisting of adjuvants, stabilizing agents, preservatives, antibacterial agents, antifungal agents, adsorption delaying agents, and any combination thereof;
   c. a container; and
   d. instructions for use of the kit components.

12. The kit of claim 11 wherein the adjuvant is selected from the group consisting of surfactants, oil, mycobacterium, immunostimulators, zinc proline, detergent, modified bacterial products, Freund's Complete Adjuvant, Freund's Incomplete Adjuvant, Gerbu Adjuvant, Ribi's Adjuvant, and any combination thereof.

13. An immunogenic composition comprising:
   a. a *Fusobacterium necrophorum* peptide sequence selected from the group consisting of SEQ ID No. 9, SEQ ID No. 12, and SEQ ID No. 15; and,
   b. a component selected from the group consisting of adjuvants, stabilizing agents, preservatives, antibacterial agents, antifungal agents, adsorption delaying agents, and any combination thereof.

14. The immunogenic composition of claim 13 wherein the adjuvant is selected from the group consisting of surfactants, oil, mycobacterium, immunostimulators, zinc proline, detergent, modified bacterial products, Freund's Complete Adjuvant, Freund's Incomplete Adjuvant, Gerbu Adjuvant, Ribi's Adjuvant, and any combination thereof.

* * * * *

SEQUENCE LISTING

<160> NUMBER OF SEQ ID NOS: 17

<210> SEQ ID NO 1
<211> LENGTH: 1071
<212> TYPE: DNA
<213> ORGANISM: Fusobacterium necrophorum

<400> SEQUENCE: 1
gaagttatgc ctgcacctat gccagaacct gaagttaaaa tcgttgaaaa acctgtcgaa      60
gttatcgttt atcgtgaccg tgtcgttcaa gcgcctgcta aatggaaacc taatgggtct     120
gttggtgttg aattaagaac tcaaggaaaa gttgaaaaca aaggtaaaaa agctactgaa     180

```
gaaaatgcaa gaaaaggttg ggctggaaaa gaacctaatg ttagattgga aacaaaagct      240
tctgtaaact tcactgaaaa tcaaaatttg gaggtaagaa caagacaaac tcatgttctt      300
actaaaacag attctgataa ggaagaatca aatcataaag atacacaagt aagaattcga      360
catacttata actttggaaa attaggttct tctaaagttg gatttaaggt agcatctcaa      420
tatttacatg atgatcatgt tgattcttta agaacaagag cagtgtttga ttttgctgat      480
tatatttata gcaatagctt attcaaaaca actgcattag aaattggtcc ttcatataaa      540
tatgtatggg gaggaaatga tgacagatat tataatgctc ttggactttta tgcaaatgca      600 gaattcgaat tgccatatgg atttggtttc caagcagaat ttgaagatgc ctttacttat      660
acttctactg gtaagggaga tggaaaaaga gataaagcta aactaggaca tgcagatttt      720
gttttatctc atagcttaga tttatataaa gaaggaaaac attctttggc tttcttaaat      780
gaattagaat atgaaacttt ctgggcttgg gataaaaaag atgctagtat ggaagaatgg      840
ccacatgttg atggacatgg aagagttaat agtgaaggaa aaaataaaaa atggggagca      900
tatgaactta cttatactcc aaaacttcaa tataactacc aagctactga attcgtaaaa      960
ttgtatgcag ctattggagg agaatacgta aatagagaaa ataataaatc aactgcacgt     1020
tactggagat ggaatccaac agcatgggct ggtatgaaag ttactttctg a              1071
```

<210> SEQ ID NO 2
<211> LENGTH: 356
<212> TYPE: PRT
<213> ORGANISM: Fusobacterium necrophorum

<400> SEQUENCE: 2

```
Glu Val Met Pro Ala Pro Met Pro Glu Pro Glu Val Lys Ile Val Glu
1               5                   10                  15

Lys Pro Val Glu Val Ile Val Tyr Arg Asp Arg Val Val Gln Ala Pro
                20                  25                  30

Ala Lys Trp Lys Pro Asn Gly Ser Val Gly Val Glu Leu Arg Thr Gln
            35                  40                  45

Gly Lys Val Glu Asn Lys Gly Lys Lys Ala Thr Glu Glu Asn Ala Arg
        50                  55                  60

Lys Gly Trp Ala Gly Lys Glu Pro Asn Val Arg Leu Glu Thr Lys Ala
65                  70                  75                  80

Ser Val Asn Phe Thr Glu Asn Gln Asn Leu Glu Val Arg Thr Arg Gln
                85                  90                  95

Thr His Val Leu Thr Lys Thr Asp Ser Asp Lys Glu Glu Ser Asn His
                100                 105                 110

Lys Asp Thr Gln Val Arg Ile Arg His Thr Tyr Asn Phe Gly Lys Leu
            115                 120                 125

Gly Ser Ser Lys Val Gly Phe Lys Val Ala Ser Gln Tyr Leu His Asp
        130                 135                 140

Asp His Val Asp Ser Leu Arg Thr Arg Ala Val Phe Asp Phe Ala Asp
145                 150                 155                 160

Tyr Ile Tyr Ser Asn Ser Leu Phe Lys Thr Thr Ala Leu Glu Ile Gly
                165                 170                 175

Pro Ser Tyr Lys Tyr Val Trp Gly Gly Asn Asp Asp Arg Tyr Tyr Asn
            180                 185                 190

Ala Leu Gly Leu Tyr Ala Asn Ala Glu Phe Glu Leu Pro Tyr Gly Phe
        195                 200                 205

Gly Phe Gln Ala Glu Phe Glu Asp Ala Phe Thr Tyr Thr Ser Thr Gly
    210                 215                 220
```

```
Lys Gly Asp Gly Lys Arg Asp Lys Ala Lys Leu Gly His Ala Asp Phe
225                 230                 235                 240

Val Leu Ser His Ser Leu Asp Leu Tyr Lys Glu Gly Lys His Ser Leu
                245                 250                 255

Ala Phe Leu Asn Glu Leu Glu Tyr Glu Thr Phe Trp Ala Trp Asp Lys
            260                 265                 270

Lys Asp Ala Ser Met Glu Glu Trp Pro His Val Asp Gly His Gly Arg
        275                 280                 285

Val Asn Ser Glu Gly Lys Asn Lys Lys Trp Gly Ala Tyr Glu Leu Thr
    290                 295                 300

Tyr Thr Pro Lys Leu Gln Tyr Asn Tyr Gln Ala Thr Glu Phe Val Lys
305                 310                 315                 320

Leu Tyr Ala Ala Ile Gly Gly Glu Tyr Val Asn Arg Glu Asn Asn Lys
                325                 330                 335

Ser Thr Ala Arg Tyr Trp Arg Trp Asn Pro Thr Ala Trp Ala Gly Met
            340                 345                 350

Lys Val Thr Phe
        355

<210> SEQ ID NO 3
<211> LENGTH: 10
<212> TYPE: PRT
<213> ORGANISM: Fusobacterium necrophorum

<400> SEQUENCE: 3

Lys Glu Val Met Pro Ala Pro Met Pro Glu
1               5                   10

<210> SEQ ID NO 4
<211> LENGTH: 12
<212> TYPE: PRT
<213> ORGANISM: Fusobacterium necrophorum

<400> SEQUENCE: 4

Lys Glu Val Met Pro Ala Pro Met Pro Glu Asp Glu
1               5                   10

<210> SEQ ID NO 5
<211> LENGTH: 12
<212> TYPE: PRT
<213> ORGANISM: Fusobacterium necrophorum

<400> SEQUENCE: 5

Lys Glu Val Met Pro Ala Pro Met Pro Glu Glu Glu
1               5                   10

<210> SEQ ID NO 6
<211> LENGTH: 26
<212> TYPE: DNA
<213> ORGANISM: Fusobacterium necrophorum

<400> SEQUENCE: 6
cgggatccag aagttatgcc tgcacc                                      26

<210> SEQ ID NO 7
<211> LENGTH: 33
<212> TYPE: DNA
<213> ORGANISM: Fusobacterium necrophorum

<400> SEQUENCE: 7
```
ggtggcggcc gcgaaagtaa ctttcatacc agc                                33

<210> SEQ ID NO 8
<211> LENGTH: 30
<212> TYPE: PRT
<213> ORGANISM: Fusobacterium necrophorum

<400> SEQUENCE: 8

Gly Lys Thr Glu Asn Lys Val Asp Gly Gln Leu Glu Lys Glu Gly Leu
 1               5                  10                  15

Gly Glu Asp Glu Leu Asp Trp Ala Arg Glu Glu Asn Asn Tyr
            20                  25                  30

<210> SEQ ID NO 9
<211> LENGTH: 17
<212> TYPE: PRT
<213> ORGANISM: Fusobacterium necrophorum

<400> SEQUENCE: 9

Val His Gly Lys Asn Pro Glu Tyr Pro Lys Ala Lys Ala Asp Lys Asp
 1               5                  10                  15

Ser

<210> SEQ ID NO 10
<211> LENGTH: 12
<212> TYPE: PRT
<213> ORGANISM: Fusobacterium necrophorum

<400> SEQUENCE: 10

Asp Gln Lys Ser Gly Asp Gly Ala Lys Lys Leu Glu
 1               5                  10

<210> SEQ ID NO 11
<211> LENGTH: 13
<212> TYPE: PRT
<213> ORGANISM: Fusobacterium necrophorum

<400> SEQUENCE: 11

Thr Asn His Arg Gly Asn Asp Arg Lys Gly Ser Glu Val
 1               5                  10

<210> SEQ ID NO 12
<211> LENGTH: 23
<212> TYPE: PRT
<213> ORGANISM: Fusobacterium necrophorum

<400> SEQUENCE: 12

Thr Phe Tyr Gly Thr Lys Gln Met Ile Ser Asp Lys Asp Gly Glu Asn
 1               5                  10                  15

Leu Arg Glu Lys Lys Arg Ala
            20

<210> SEQ ID NO 13
<211> LENGTH: 22
<212> TYPE: PRT
<213> ORGANISM: Fusobacterium necrophorum

<400> SEQUENCE: 13

Pro Tyr Ser Phe His Gln Tyr Arg Ser Tyr Asp Lys Lys Thr Glu Asp
 1               5                  10                  15

Val Gly Ala Lys Arg Ser
            20

```
<210> SEQ ID NO 14
<211> LENGTH: 12
<212> TYPE: PRT
<213> ORGANISM: Fusobacterium necrophorum

<400> SEQUENCE: 14

Asn Trp Lys Val Lys Asp Glu Asp Tyr Ala Thr Arg
1               5                   10

<210> SEQ ID NO 15
<211> LENGTH: 51
<212> TYPE: PRT
<213> ORGANISM: Fusobacterium necrophorum

<400> SEQUENCE: 15

Asn Asn Tyr Gly Arg Leu Gln Thr Glu Ala Lys Ile Asn Phe Thr Glu
1               5                   10                  15

Asn Gln Lys Leu Glu Val Arg Thr Arg Asn Phe His Thr Trp Val His
            20                  25                  30

Gly Lys Asn Pro Glu Tyr Pro Lys Ala Lys Ala Asp Lys Asp Ser Val
        35                  40                  45

Arg Leu Arg
    50

<210> SEQ ID NO 16
<211> LENGTH: 42
<212> TYPE: PRT
<213> ORGANISM: Fusobacterium necrophorum

<400> SEQUENCE: 16

Pro Lys Ala Lys Ala Asp Lys Asp Ser Val Arg Leu Arg His Phe Tyr
1               5                   10                  15

Asn Phe Gly Lys Ile Ala Asp Thr Lys Val Asn Ala Thr Ser Arg Leu
            20                  25                  30

Glu Trp Asp Gln Lys Ser Gly Asp Gly Ala
        35                  40

<210> SEQ ID NO 17
<211> LENGTH: 60
<212> TYPE: PRT
<213> ORGANISM: Fusobacterium necrophorum

<400> SEQUENCE: 17

Arg Val Val Gln Ala Pro Ala Lys Trp Lys Pro Asn Gly Ser Ile Asp
1               5                   10                  15

Val Gln Tyr Arg Trp Tyr Gly Lys Thr Glu Asn Lys Val Asp Gly Gln
            20                  25                  30

Leu Glu Lys Glu Gly Leu Gly Glu Asp Glu Leu Asp Trp Ala Arg Glu
        35                  40                  45

Glu Asn Asn Tyr Gly Arg Leu Gln Thr Glu Ala Lys
    50                  55                  60
```